United States Patent
Bai et al.

(10) Patent No.: US 10,162,933 B2
(45) Date of Patent: Dec. 25, 2018

(54) HIGH RESOLUTION ALLELE IDENTIFICATION

(71) Applicant: Regeneron Pharmaceuticals, Inc., Tarrytown, NY (US)

(72) Inventors: Yu Bai, Scarsdale, NY (US); Wen Fury, New York, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 833 days.

(21) Appl. No.: 14/513,952

(22) Filed: Oct. 14, 2014

(65) Prior Publication Data

US 2015/0110754 A1  Apr. 23, 2015

Related U.S. Application Data

(60) Provisional application No. 61/891,193, filed on Oct. 15, 2013.

(51) Int. Cl.
| | | |
|---|---|---|
| *G06F 19/22* | (2011.01) | |
| *C12Q 1/6881* | (2018.01) | |
| *G06F 19/18* | (2011.01) | |

(52) U.S. Cl.
CPC ........... *G06F 19/22* (2013.01); *C12Q 1/6881* (2013.01); *G06F 19/18* (2013.01); *C12Q 2600/156* (2013.01)

(58) Field of Classification Search
None
See application file for complete search history.

(56) References Cited

U.S. PATENT DOCUMENTS

2010/0256917 A1  10/2010  McVean et al.

OTHER PUBLICATIONS

Bai, Y. et al., "Inference of High Resolution HLA Types Using Genome-wide RNA or DNA Sequencing Reads," BMC Gemonics, 15:325 (2014).
Boegel, S. et al., "HLA Typing From RNA-Seq Sequence Reads," Genome Medicine, 4:102 (2012).
Kim, J. H. et al., "HLA Haplotyping from RNA-seq Data Using Hierarchical Read Weighting," PLOS, 8(6):e67885 (2013).
Warren, R.L. et al., "Derivation of HLA Types from Shotgun Sequence Datasets," Genome Medicine, 4:95 (2012).
PCT, PCT/IB14/002843 (WO 2015/056103), filed Oct. 14, 2014, Bai (Regeneron Pharma., Inc.).
Communication Pursuant to Article 94(3) EPC dated Mar. 27, 2017 by the European Patent Office for European Patent Application No. 14843178.6, which was filed Oct. 14 ,2014 and published as 3058095 dated Aug. 24, 2016 (Inventor-Bai et al.; Applicant-Regeneron Pharmaceuticals, Inc.) (5 pages).
Preliminary Report on Patentability dated Apr. 19, 2016 by the International Searching Authority for International Patent Application No. PCT/IB2014/002843, which was filed Oct. 14, 2014 and published as WO 2015/056103 dated Apr. 23, 2015 (Inventor-Bai et al.; Applicant-Regeneron Pharmaceuticals, Inc.) (15 pages).
Notification of Reasons for Refusal was dated Oct. 18, 2018 by the Japanese Patent Office for JP Application No. 2016-523227, which was filed on Oct. 14, 2014 and published as JP2016-541043 dated Dec. 28, 2016 (Applicant-Regeneron Pharmaceuticals, Inc.) (Original-4 pages//Translation-3 pages).

*Primary Examiner* — Joseph Woitach
(74) *Attorney, Agent, or Firm* — Ballard Spahr LLP

(57) ABSTRACT

Provided herein are methods for accurately determining the alleles present at a locus that is broadly applicable to any locus, including highly polymorphic loci such as HLA loci, BGA loci and HV loci. Embodiments of the disclosed methods are useful in a wide range of applications, including, for example, organ transplantation, personalized medicine, diagnostics, forensics and anthropology.

24 Claims, 8 Drawing Sheets
Specification includes a Sequence Listing.

Figure 3

| HLA Resolution | Dataset | PHLAT accuracy | *HLAminer accuracy | HLAforest accuracy | †seq2HLA accuracy |
|---|---|---|---|---|---|
| 4-digit | HapMap RNAseq | 92.3% | 39.8% | 84.2% | #32% |
| | 1000Genome WXS | 95.0% | 55.0% | 77.0% | - |
| | HapMap WXS | 93.3% | 53.3% | 45.6% | - |
| | Amplicon seq | 100% | 50.0% | - | - |
| 2-digit | HapMap RNAseq | 99.1% | 71.1% | 97.3% | 97.1% |
| | 1000Genome WXS | 97.0% | 83.0% | 95.0% | 90.0% |
| | HapMap WXS | 95.6% | 78.9% | 81.1% | 93.3% |
| | Amplicon seq | 100% | 95.0% | - | - |

Figure 5

Primers and protocol schema used in targeted amplicon sequencing of HLA-A and B loci

| Oligo Name | Oligo Sequences | Oligo Names |
|---|---|---|
| OEM51 | CRGGTCTCAGCCACTSCTC | I-HLA-A, Exon 2-5' |
| OEM52 | CTCGGACCCGGAGACTGT | I-HLA-A, Exon 2-3' |
| OEM57 | CTYGGGGGACYGGGCTGAC | I-HLA-A, Exon 3-5' |
| OEM58 | CCCAATTGTCTCCCCTCCTTG | I-HLA-A, Exon 3-3' |
| OEM59 | GGSAGGGAAATGGCCTCT | I-HLA-B, Exon 2-5' |
| OEM60 | GGATGGGGAGTCGTGACCT | I-HLA-B, Exon 2-3' |
| OEM55 | GCGTTTACCGGTTTCATT | I-HLA-B, Exon 3-5' |
| OEM56 | CGGCGACCTATAGGAGATGG | I-HLA-B, Exon 3-3' |
| OEM49 | CTACACGACGCTCTTCCGATCT NNNN CRGGTCTCAGCCACTSCTC | II-HLA-A, Exon 2-5' |
| OEM50 | CAGACGTGTGCTCTTCCGATCT CTCGGACCCGGAGACTGT | II-HLA-A, Exon 2-3' |
| OEM65 | CTACACGACGCTCTTCCGATCT NNNN CTYGGGGGACYGGGCTGAC | II-HLA-A, Exon 3-5' |
| OEM66 | CAGACGTGTGCTCTTCCGATCT CCCAATTGTCTCCCCTCCTTG | II-HLA-A, Exon 3-3' |
| OEM67 | CTACACGACGCTCTTCCGATCT NNNN GGSAGGGAAATGGCCTCT | II-HLA-B, Exon 2-5' |
| OEM68 | CAGACGTGTGCTCTTCCGATCT GGATGGGGAGTCGTGACCT | II-HLA-B, Exon 2-3' |
| OEM53 | CTACACGACGCTCTTCCGATCT NNNN GCGTTTACCGGTTTCATT | II-HLA-B, Exon 3-5' |
| OEM54 | CAGACGTGTGCTCTTCCGATCT CGGCGACCTATAGGAGATGG | II-HLA-B, Exon 3-3' |
| OEM14 | AATGATACGGCGACCACCGA GATCT ACACTCTTTCCCTAC ACGACGCTCTTCCGATCT | III 5' |
| ScriptSeq REGN91 | CAAGCAGAAGACGGCATACGAGAT GATTAGCC GTGACTGGAGTTCAGACGTGTGCTCTTCCGATCT | III 3'-REGN91 |
| ScriptSeq REGN92 | CAAGCAGAAGACGGCATACGAGAT TGCGACAT GTGACTGGAGTTCAGACGTGTGCTCTTCCGATCT | III 3'-REGN92 |
| ScriptSeq REGN93 | CAAGCAGAAGACGGCATACGAGAT CAGCGTTA GTGACTGGAGTTCAGACGTGTGCTCTTCCGATCT | III 3'-REGN93 |
| ScriptSeq REGN94 | CAAGCAGAAGACGGCATACGAGAT TCCGTAAG GTGACTGGAGTTCAGACGTGTGCTCTTCCGATCT | III 3'-REGN94 |
| ScriptSeq REGN95 | CAAGCAGAAGACGGCATACGAGAT ATGGTACC GTGACTGGAGTTCAGACGTGTGCTCTTCCGATCT | III 3'-REGN95 |

HIGH RESOLUTION ALLELE IDENTIFICATION

RELATED APPLICATIONS

This application claims the benefit of priority to Provisional Application No. 61/891,193, filed Oct. 15, 2013, which is hereby incorporated by reference in its entirety.

BACKGROUND

While most of the human genome is made up of conserved sequences shared by essentially the entire human population, a small but significant fraction of the genome is highly variable. These sequence differences are not evenly spread across the genome. Rather, certain genomic regions ("loci") contain many more sequence variations ("polymorphisms") than others. The identity of the specific nucleotide sequence at a particular locus (i.e., the allele present at that locus) can have significant biological implications. For example, the allele an individual carries at a particular locus can influence whether an individual is susceptible to a disease or whether a therapeutic agent is likely to be efficacious. In addition, knowledge of the identity of the alleles at a highly polymorphic locus can be used to track the ethnic and/or geographic origins of a biological sample, which can be invaluable to anthropologist and can be used forensically to link an individual with a biological sample. Given the increasing availability next-generation sequencing technology, the prospect of using next-generation sequencing data for allele identification is attractive. Unfortunately, accurately and efficiently identifying the alleles present at highly polymorphic loci using sequencing data is challenging, particularly when the sequencing data are generated using high-throughput genome-wide sequencing methods.

One set of highly-polymorphic loci for which there is a need for highly accurate allele prediction processes are those that encode Human Leukocyte Antigen (HLA) proteins. HLA proteins present antigen peptides to lymphocytes in order to mediate key immunological events, including self-antigen tolerance and immune responses to pathogens or tumors. Class I HLAs are ubiquitously expressed by all nucleated cells and present cytosolic antigens to cytotoxic T cells. Class II HLAs are primarily expressed by immune cells and present extracellular antigens to helper T cells.

Humans have six major HLA proteins, three class I proteins (HLA-A, HLA-B and HLA-C) and three class II proteins (HLA-DQ, HLA-DR and HLA-DP). Each class I protein is encoded by a single HLA locus (e.g., the HLA-A locus, the HLA-B locus and the HLA-C locus). The class II proteins, on the other hand, are heterodimers made up of an a chain and a 13 chain, each of which is encoded by its own HLA locus (e.g., the HLA-DQA1 locus, the HLA-DQB1 locus, the HLA-DRA locus, the HLA-DRB1 locus, the HLA-DRB3 locus, the HLA-DRB4 locus, the HLA-DRB5 locus, the HLA-DPA1 locus and the HLA-DPB1 locus). In humans, each of the major HLA loci (both class I and class II) are present on chromosome 6. Being diploid organisms, humans carry two copies of chromosome 6, and therefore carry two copies of each HLA locus.

HLA loci are highly polymorphic. Polymorphisms in the HLA loci often result in differences in the amino acid sequences of HLA proteins. This HLA diversity allows a wide range of different antigens to be presented to immune cells within a population. However, these variations in HLA sequence also result in histoincompatibility of organs and tissues between individuals, greatly complicating surgical transplantation procedures. If the HLA proteins expressed by a transplanted organ or tissue are recognized as foreign by the transplant recipient's immune system, the likely result is organ rejection. Similarly, a transplantation that includes the transfer of immune cells that recognize as foreign the HLA proteins expressed by cells in the transplant recipient can result in graft versus host disease. The risk of graft-versus-host disease and organ or tissue rejection can be minimized if the alleles present at the HLA loci of a perspective donor and recipient encode matching HLA proteins, to the greatest extent possible. In order to determine whether there is a match, it is necessary to determine what HLA alleles are present at HLA loci in the donor and recipient, a process known as HLA typing. An individual's HLA type at an HLA locus is made up of the two HLA alleles (or the two copies of a single HLA allele if homozygous) present at the individual's two copies of the HLA locus.

HLA types are also increasingly recognized to play a significant role in numerous diseases. For instance, there are strong associations between certain HLA types and autoimmune disorders, including lupus, inflammatory bowel diseases, multiple sclerosis, arthritis and type I diabetes (e.g., Graham et al., *Eur. Hum. Genet.* 15:823-830 (2007); Fu et al., *J. Autoimmun.* 37:104-112 (2011); Cassinotti et al., *Am. J. Gastroenterol* 104:195-217 (2009); Luckey et al., *J. Autoimmun.* 37:122-128 (2011); Lemire, M., BMC Proc. 7:S33 (2009); Noble et al., Curr. Diab. Rep. 11:533-542 (2011), each of which is hereby incorporated by reference in its entirety). As one example, class II HLA DQA1*02:01 (DQ2) and DRB1*03:01(DR3) are frequently present in systemic lupus erythematosus patients and are significantly associated with disease susceptibility (Graham et al., *Eur. Hum. Genet.* 15:823-830 (2007)). Presence of other class II HLA proteins also correlate with either the resistance or susceptibility to breast and cervical cancers (e.g., Chaudhuri et al., *Proc. Nuc. Acad. Sci. USA* 97:11451-11454 (2000); Garcia-Corona et al., *Arch. Dermatol.* 140:1227-1231 (2004), each of which is hereby incorporated by reference in its entirety).

The pathogenesis and therapeutic indications of HLA molecules highlight the need for accurate and efficient methods of HLA typing. In the past, HLA types have been resolved at low resolution by distinguishing "two-digit" antigen groups that approximate serologic specificities in peptide binding. However, for many applications, two-digit HLA typing is insufficient. For example, a single amino acid difference between two HLA proteins of the same two-digit type can result in altered T-cell recognition specificity and tissue rejection (e.g., Archbold et al., *Trends. Immunol.* 29:220-226 (2008); Tynan et al., *Nat. Immunol.* 6:1114-1122 (2005); Fleischhauer et al., *N Eng. J. Med.* 323:1818-1822 (1990), each of which is hereby incorporated by reference in its entirety). Consequently, high-resolution HLA typing at the amino acid sequence level (known as "four-digit" typing) can be critical. For example, resolving HLA types at high-resolution substantially improves the clinical outcome in unrelated cord blood transplantation and in cancer vaccination trials (Nagorson et al., *Cancer Immunol. Immunother.* 57:1903-1910 (2008); Liao et al., *Bone Marrow Transplant.* 40:201-208 (2007), each of which is hereby incorporated by reference in its entirety).

The highly polymorphic nature of HLA loci renders accurate, high-resolution typing a considerable challenge, particularly at high throughput. More than 7527 four-digit HLA alleles are present at the major class I and class II HLA loci in the human population. Existing HLA typing methodologies capable of resolving HLA types at four-digit resolution, such as group specific PCR by sequencing specific priming (SSP) and sequence-based typing (SBT), have low throughput. Other proposed typing strategies specifically target the HLA loci via PCR-amplification, followed by deep sequencing. Such methods require long reads and a high coverage (depth) in order to produce accurate assignment of four-digit HLA alleles. Due to cost and efficiency considerations, genome-wide sequencing, such as transcriptome or whole exome/genome sequencing, generally produce much shorter reads (<100 bases) and lower coverage. These read length and coverage limitations reduce the accuracy of current methodologies that attempt to use genome-wide sequencing processes for HLA typing. Specifically, the four-digit HLA type identification accuracy of current methods using short read sequencing has been reported to be between 32% and 84% (e.g., Boegel et al., *Genome Med.* 4:102 (2013); Kim and Pourmand *PLoS One* 8:e67885 (2013)).

In light of the foregoing, there is a need for new methods of accurately and efficiently identifying the alleles present at a locus using diverse sequencing data, including data with short read lengths and low sequence coverage.

SUMMARY

In aspects, provided herein are methods (including computer implemented methods), computer programs and computer systems for accurately determining the alleles present at a locus (e.g., determining the HLA type at an HLA locus). Also provided herein are methods for transplanting an organ, tissue or cell, methods for preventing transplant rejection and/or methods for preventing graft versus host disease.

In some aspects, provided herein is a computer-implemented method for determining the alleles at one or more loci (e.g., in a subject, sample, organ, tissue and/or cell). In some embodiments, the locus is an HLA locus. In some embodiments, the locus is a mitochondrial hypervariable region (HV) locus (e.g., an HV1 locus or an HV2 locus). In some embodiments, the locus is a blood group antigen (BGA) locus. In some embodiments, the locus is a moderately polymorphic locus (i.e., a locus that averages at least 1 SNP per 100 nucleotides of length), a highly polymorphic locus (i.e. a locus that averages at least 1 SNP per 20 nucleotides of length), or a very highly polymorphic locus (i.e., a locus that averages at least 1 SNP per 10 nucleotides of length).

In some embodiments, the locus contains on average per 100 bases: 1 or more but less than 20 SNPs, 2 or more but less than 20 SNPs, 3 or more but less than 20 SNPs, 4 or more but less than 20 SNPs, 5 or more but less than 20 SNPs, 6 or more but less than 20 SNPs, 7 or more but less than 20 SNPs, 8 or more but less than 20 SNPs, 9 or more but less than 20 SNPs, 10 or more but less than 20 SNPs, 11 or more but less than 20 SNPs, 12 or more but less than 20 SNPs, 13 or more but less than 20 SNPs, 14 or more but less than 20 SNPs, 15 or more but less than 20 SNPs, 16 or more but less than 20 SNPs, 17 or more but less than 20 SNPs, 18 or more but less than 20 SNPs, or 19 or more but less than 20 SNPs.

In various embodiments, the moderately polymorphic locus contains on average per 100 bases: 1 or more but less than 5 SNPs, 2 or more but less than 5 SNPs, 3 or more but less than 5 SNPs, or 4 or more but less than 5 SNPs. In various embodiments, the moderately polymorphic locus contains on average per 100 bases: about 1-2 SNPs, 2-3 SNPs, or about 3-4 SNPs.

In various embodiments, the highly polymorphic locus contains on average per 100 bases: 5 or more but less than 10 SNPs, 6 or more but less than 10 SNPs, 7 or more but less than 10 SNPs, 8 or more but less than 10 SNPs, 9 or more but less than 10 SNPs per 100 nucleotides of length. In various embodiments, the highly polymorphic locus contains in on average per 100 bases: about 5-6 SNPs, about 6-7 SNPs, about 7-8 SNPs, or about 8-9 SNPs.

In various embodiments, the very highly polymorphic locus contains on average per 100 bases: 10 or more but less than 20 SNPs, 11 or more but less than 20 SNPs, 12 or more but less than 20 SNPs, 13 or more but less than 20 SNPs, 14 or more but less than 20 SNPs, 15 or more but less than 20 SNPs, 16 or more but less than 20 SNPs, 17 or more but less than 20 SNPs, 18 or more but less than 20 SNPs, or 19 or more but less than 20 SNPs. In one embodiment, the very highly polymorphic locus contains on average per 100 bases: about 10-11 SNPs, about 11-12 SNPs, about 12-13 SNPs, about 13-14 SNPs, about 14-15 SNPs, about 15-16 SNPs, about 16-17 SNPs, about 17-18 SNPs, or about 18-19 SNPs. In one embodiment, the very highly polymorphic locus contains on average per 100 bases about 20 SNPs.

In some embodiments, the computer-implemented method includes: a) receiving sequence data at a computer system, the sequence data comprising a plurality of sequencing reads; b) mapping, by the computer system, the sequencing reads to a reference sequence comprising a plurality of alleles of the locus to identify candidate alleles; and c) identifying, by the computer system, the pair of candidate alleles with the greatest likelihood of accounting for the sequencing reads that map to the locus as the alleles that are present at the locus. In some embodiments, the alleles are HLA alleles, HV alleles or BGA alleles and the locus is an HLA locus, an HV locus or a BGA locus. In some embodiments, the alleles that are present at the locus make up the HLA type at the locus. In some embodiments, the reference sequence also includes a genome sequence (e.g., a genome sequence with the locus masked or removed). In some embodiments, the alleles and sequences are human.

In some embodiments, step b) of the above method includes the steps, performed by the computer system, of: i) mapping the sequencing reads to a reference sequence, the reference sequence comprising a genome sequence and a plurality of allele sequences of the locus; ii) identifying as a first set of candidate alleles the alleles to which map the greatest number of sequencing reads; iii) identifying as a second set of candidate alleles the alleles to which map the greatest number of sequencing reads, excluding the sequencing reads that map to the first set of candidate alleles; and iv) if less than 90% of the sequencing reads that map to the locus map to an allele of the first or second set of candidate alleles, identifying as a third set of candidate alleles the alleles to which map the greatest number of sequencing reads, excluding the reads that map to the first or second set of candidate alleles. In some embodiments, the identified alleles are selected from a set of protein groups. The term "protein group" includes a set of alleles that encode the same protein with identical amino acid sequences. In some embodiments, the second set of candidate alleles includes both the alleles to which map the greatest number of sequencing reads excluding the sequencing reads that map to the first set of candidate alleles, and the alleles to which map the second greatest number of sequencing reads, without excluding the sequencing reads that map to the first set of candidate alleles, if the sequencing reads that map to the locus, excluding the sequencing reads that map to the first set of candidate alleles, are greater than 1% of the number of sequencing reads that map to the first set of candidate alleles. In some embodiments, the third set of candidate alleles are only identified in step iv) if the number of sequencing reads that map to the alleles to which map the greatest number of sequencing reads, excluding the reads that map to the first or second set of candidate alleles, make up at least 10% of the total number of sequencing reads that map to the locus.

In some embodiments, step b) of the above method includes the steps, performed by the computer system, of: i) mapping the sequencing reads to a reference sequence at a low stringency, the reference sequence comprising a human genome sequence and a plurality of allele sequences of the locus; ii) identifying as pre-candidate alleles all alleles from each four-digit protein families for which at least one allele was among the top 10% of alleles mapped; iii) mapping the sequencing reads to a reference sequence at a higher stringency, the reference sequence comprising the pre-candidate alleles; iv) identifying as a first set of candidate alleles the pre-candidate alleles to which map the greatest number of sequencing reads; v) identifying as a second set of candidate alleles the pre-candidate alleles to which map the greatest number of sequencing reads, excluding the sequencing reads that map to the first set of candidate alleles; and vi) if less than 90% of the sequencing reads that map to the locus map to an allele of the first or second set of candidate alleles, identifying as a third set of candidate alleles the pre-candidate alleles to which map the greatest number of sequencing reads, excluding the reads that map to the first or second set of candidate alleles. In some embodiments, the identified alleles are selected from a set of protein groups. In some embodiments, the second set of candidate alleles includes both the alleles to which map the greatest number of sequencing reads, excluding the sequencing reads that map to the first set of candidate alleles, and the alleles to which map the second greatest number of sequencing reads, without excluding the sequencing reads that map to the first set of candidate alleles, if the sequencing reads that map to the locus, excluding the sequencing reads that map to the first set of candidate alleles, are greater than 1% of the number of sequencing reads that map to the first set of candidate alleles. In some embodiments, the third set of candidate alleles are only identified if the number of sequencing reads that map to the HLA alleles to which map the greatest number of sequencing reads, excluding the reads that map to the first or second set of candidate alleles, make up at least 10% of the total number of sequencing reads that map to the HLA locus.

In some embodiments, the pair of candidate alleles with the greatest likelihood of accounting for the sequencing reads is the pair of candidate alleles that have the greatest likelihood of accounting for: i) individual single nucleotide polymorphisms (SNPs) present in the sequencing reads that map to the candidate alleles; and ii) the sequential pairs of SNPs present in the sequencing reads that map to the candidate alleles. In some embodiments, the pair of candidate alleles with the greatest likelihood of accounting for the sequencing reads is the pair of candidate alleles that have the greatest likelihood of accounting for: i) individual SNPs present in the sequencing reads that map to the candidate alleles; ii) the sequential pairs of SNPs present in the sequencing reads that map to the candidate alleles; and iii) the frequency of the pair of candidate alleles in the organism from which the sequence data originated (e.g., in humans).

In some embodiments, the pair of candidate alleles with the greatest likelihood of accounting for the sequencing reads is determined by: i) for each pair of candidate alleles, determining genotype log-likelihood scores for each individual SNP in the locus, each genotype log-likelihood score being the sum of the log-probabilities for each individual SNP in the locus that the pair of candidate alleles could account for the sequences present at the individual SNP in the sequencing reads that map to the SNP; and ii) for each pair of candidate alleles, determining phase log-likelihood scores for each sequential pair of SNPs in the locus, each phase log-likelihood score being the sum of the log-probabilities for each sequential pair of SNPs in the locus that the pair of candidate alleles could account for the sequences present at the sequential pair of SNPs in the sequencing reads that map to the sequential pair of SNPs, wherein the pair of candidate alleles for which the sum of the genotype log-likelihood scores and the phase log-likelihood scores is highest is the pair of candidate alleles with the greatest likelihood of accounting for the sequencing reads.

In some embodiments, the pair of candidate alleles with the greatest likelihood of accounting for the sequencing reads is determined by: i) for each pair of candidate alleles, determining genotype log-likelihood scores for each individual SNP in the locus, each genotype log-likelihood score being the sum of the log-probabilities for each individual SNP in the locus that the pair of candidate alleles could account for the sequences present at the individual SNP in the sequencing reads that map to the SNP; ii) for each pair of candidate alleles, determining phase log-likelihood scores for each sequential pair of SNPs in the locus, each phase log-likelihood score being the sum of the log-probabilities for each sequential pair of SNPs in the locus that the pair of candidate alleles could account for the sequences present at the sequential pair of SNPs in the sequencing reads that map to the sequential pair of SNPs; and iii) for each pair of candidate alleles, determining a frequency log-likelihood score, the frequency log-likelihood score being the sum of the log-frequencies at which each of the pair of candidate alleles are present in the human population, wherein the pair of candidate alleles for which the sum of the genotype log-likelihood scores, the phase log-likelihood scores and the frequency log-likelihood score is highest is the pair of candidate alleles with the greatest likelihood of accounting for the sequencing reads.

In some aspects, provided herein is a computer-implemented method which includes: a) receiving sequence data at a computer system, the sequence data comprising a plurality of sequencing reads; b) mapping, by the computer system, the sequencing reads to a reference sequence, the reference sequence comprising a genome sequence and a plurality of allele sequences of the locus; d) identifying, by the computer system, as a first set of candidate alleles the alleles to which map the greatest number of sequencing reads; e) if less than 90% of the sequencing reads that map to the locus map to an allele of the first or second set of candidate alleles, identifying, by the computer system, as a third set of candidate alleles the alleles to which map the greatest number of sequencing reads excluding the reads that map to the first or second set of candidate alleles; f) for each pair of candidate alleles, determining, by the computer system, genotype log-likelihood scores for each individual SNP in the locus, each genotype log-likelihood score being the sum of the log-probabilities for each individual SNP in the locus that the pair of candidate alleles could account for the sequences present at the individual SNP in the sequencing reads that map to the SNP; g) for each pair of candidate alleles, determining, by the computer system, phase log-likelihood scores for each sequential pair of SNPs in the locus, each phase log-likelihood score being the sum of the log-probabilities for each sequential pair of SNPs in the locus that the pair of candidate alleles could account for the sequences present at the sequential pair of SNPs in the sequencing reads that map to the sequential pair of SNPs; h) for each pair of candidate alleles, determining, by the computer system, a frequency log-likelihood score, the frequency log-likelihood score being the sum of the log-frequencies at which each of the pair of candidate alleles are present in the human population; and i) identifying, by the computer system, the pair of candidate alleles having the highest sum of the genotype log-likelihood score, the phase log-likelihood score, and the frequency log-likelihood score as the alleles present at the locus. In some embodiments, the identified alleles are selected from a set of protein groups. In some embodiments, the second set of candidate alleles includes both the alleles to which map the greatest number of sequencing reads, excluding the sequencing reads that map to the first set of candidate alleles, and the alleles to which map the second greatest number of sequencing reads, without excluding the sequencing reads that map to the first set of candidate alleles, if the sequencing reads that map to the locus, excluding the sequencing reads that map to the first set of candidate alleles, are greater than 1% of the number of sequencing reads that map to the first set of candidate alleles. In some embodiments, the alleles are HLA alleles, HV alleles or BGA alleles and the locus is an HLA locus, an HV locus or a BGA locus. In some embodiments, the alleles that are present at the locus make up the HLA type at the locus. In some embodiments the alleles and sequences are human. In some embodiments, the third set of candidate alleles are only identified in step e) if the number of sequencing reads that map to the alleles to which map the greatest number of sequencing reads, excluding the reads that map to the first or second set of candidate alleles, make up at least 10% of the total number of sequencing reads that map to the locus.

In some embodiments of the computer-implemented methods provided herein, the sequence data are genome-wide sequencing data. In some embodiments, the genome-wide sequencing data are transcriptome sequencing data, whole exome sequencing data, or whole genome sequencing data. In some embodiments, the coverage of the sequence data is less than 60 fold, 50 fold, 40 fold, 30 fold, 20 fold or 15 fold. In some embodiments, the coverage of the sequence data is greater than 60 fold. In some embodiments, the average length of the sequencing reads is less than 100, 90, 80, 70, 60, 50, 45, 40 or 35 nucleotides. In some embodiments, the length of the sequencing reads is greater than 100 nucleotides.

In certain embodiments of the computer-implemented methods provided herein, the reference sequence includes a human genome sequence. In some embodiments, the sequence of the locus (e.g., the HLA locus) in the genome sequence has been removed or masked. In some embodiments, the human genome sequence is GRCh37/hg19.

In some embodiments, the methods described herein include the step of performing a genome-wide sequencing process on a sample to generate the sequence data. In some embodiments, the methods described herein include performing a nucleic acid amplification process that produces an amplification product that comprises a nucleic acid sequence of the locus and performing a sequencing process on the amplification product.

In some embodiments, the methods provided herein include the step of transplanting, to a recipient, a cell, tissue or organ having an HLA type at an HLA locus that matches an HLA type of the subject at the HLA locus. In some embodiments, a computer-implemented method provided herein is performed to determine the HLA type of the recipient at the HLA locus. In some embodiments, a computer-implemented method provided herein is performed to determine the HLA type of the cell, tissue or organ at the HLA locus. In some embodiments, a computer-implemented method provided herein is performed to determine the HLA type at the HLA locus of both the cell, tissue or organ and the recipient.

In some aspects, provided herein is a computer system for performing a computer-implemented method provided herein. In some embodiments, the computer system includes: at least one processor; memory associated with the at least one processor; a display; and a program supported in the memory for determining alleles at a locus (e.g., the HLA type at an HLA locus), the program containing a plurality of instructions which, when executed by the at least one processor, cause the at least one processor to perform a computer-implemented method provided herein. In some embodiments, the instructions, when executed by at least one processor, cause the at least one processor to: a) receive sequence data, the sequence data comprising a plurality of sequencing reads; b) map the sequencing reads to a reference sequence comprising a plurality of alleles of the locus to identify candidate alleles; and c) identify the pair of candidate alleles with the greatest likelihood of accounting for the sequencing reads that map to the locus as the alleles present at the locus. In some embodiments, the instructions, when executed by at least one processor, cause the at least one processor to: a) receive sequence data, the sequence data comprising a plurality of sequencing reads; b) map the sequencing reads to a reference sequence, the reference sequence comprising a human genome sequence and a plurality of allele sequences of the locus; c) identify as a first set of candidate alleles the alleles to which map the greatest number of sequencing reads; d) identify as a second set of candidate alleles the alleles to which map the greatest number of sequencing reads, excluding the sequencing reads that map to the first set of candidate alleles; e) if less than 90% of the sequencing reads that map to the locus map to an allele of the first or second set of candidate alleles, identify as a third set of candidate alleles the alleles to which map the greatest number of sequencing reads excluding the reads that map to the first or second set of candidate alleles; f) for each pair of candidate alleles, determine genotype log-likelihood scores for each individual SNP in the locus, each genotype log-likelihood score being the sum of the log-probabilities for each individual SNP in the locus that the pair of candidate alleles could account for the sequences present at the individual SNP in the sequencing reads that map to the SNP; g) for each pair of candidate alleles, determine phase log-likelihood scores for each sequential pair of SNPs in the locus, each phase log-likelihood score being the sum of the log-probabilities for each sequential pair of SNPs in the locus that the pair of candidate alleles could account for the sequences present at the sequential pair of SNPs in the sequencing reads that map to the sequential pair of SNPs; h) for each pair of candidate alleles, determine a frequency log-likelihood score, the frequency log-likelihood score being the sum of the log-frequencies at which each of the pair of candidate alleles are present in the human population; and i) identify the pair of candidate alleles having the highest sum of the genotype log-likelihood score, the phase log-likelihood score, and the frequency log-likelihood score as the alleles present at the locus. In some embodiments, the identified alleles are selected from a set of protein groups. In some embodiments, the alleles are HLA alleles, HV alleles or BGA alleles and the locus is an HLA locus, an HV locus or a BGA locus. In some embodiments, the second set of candidate alleles includes both the alleles to which map the greatest number of sequencing reads, excluding the sequencing reads that map to the first set of candidate alleles, and the alleles to which map the second greatest number of sequencing reads, without excluding the sequencing reads that map to the locus, excluding the sequencing reads that map to the first set of candidate alleles, are greater than 1% of the number of sequencing reads that map to the first set of candidate alleles. In some embodiments, the third set of candidate alleles are only identified if the number of sequencing reads that map to the alleles to which map the greatest number of sequencing reads, excluding the reads that map to the first or second set of candidate alleles, make up at least 10% of the total number of sequencing reads that map to the locus. In some embodiments, the alleles that are present at the locus make up the HLA type at the locus. In some embodiments, the reference sequence also includes a genome sequence (e.g., a genome sequence with the locus masked or removed). In some embodiments the alleles and sequences are human.

In some aspects, provided herein is a computer program product for determining the alleles present at a locus. In some embodiments, the computer program product resides on a non-transitory computer readable medium having a plurality of instructions stored thereon which, when executed by a computer processor, cause that computer processor to perform a computer-implemented method provided herein. In certain embodiments, the plurality of instructions, when executed by a computer processor, cause the computer processor to: a) receive sequence data, the sequence data comprising a plurality of sequencing reads; b) map the sequencing reads to a reference sequence comprising a plurality of alleles of the locus to identify candidate alleles; and c) identify the pair of candidate alleles with the greatest likelihood of accounting for the sequencing reads that map to the locus as the alleles present at the locus. In certain embodiments, the plurality of instructions, when executed by a computer processor, cause the computer processor to: a) receive sequence data, the sequence data comprising a plurality of sequencing reads; b) map the sequencing reads to a reference sequence, the reference sequence comprising a human genome sequence and a plurality of allele sequences of the locus; c) identify as a first set of candidate alleles the alleles to which map the greatest number of sequencing reads; d) identify as a second set of candidate alleles the alleles to which map the greatest number of sequencing reads, excluding the sequencing reads that map to the first set of candidate alleles; e) if less than 90% of the sequencing reads that map to the locus map to an allele of the first or second set of candidate alleles, identify as a third set of candidate alleles the alleles to which map the greatest number of sequencing reads excluding the reads that map to the first or second set of candidate alleles; f) for each pair of candidate alleles, determine genotype log-likelihood scores for each individual SNP in the locus, each genotype log-likelihood score being the sum of the log-probabilities for each individual SNP in the locus that the pair of candidate alleles could account for the sequences present at the individual SNP in the sequencing reads that map to the SNP; g) for each pair of candidate alleles, determine phase log-likelihood scores for each sequential pair of SNPs in the locus, each phase log-likelihood score being the sum of the log-probabilities for each sequential pair of SNPs in the locus that the pair of candidate alleles could account for the sequences present at the sequential pair of SNPs in the sequencing reads that map to the sequential pair of SNPs; h) for each pair of candidate alleles, determine a frequency log-likelihood score, the frequency log-likelihood score being the sum of the log-frequencies at which each of the pair of candidate alleles are present in the human population; and i) identify the pair of candidate alleles having the highest sum of the genotype log-likelihood score, the phase log-likelihood score, and the frequency log-likelihood score as the alleles present at the locus. In some embodiments, the identified alleles are selected from a set of protein groups. In some embodiments, the second set of candidate alleles includes both the alleles to which map the greatest number of sequencing reads, excluding the sequencing reads that map to the first set of candidate alleles, and the alleles to which map the second greatest number of sequencing reads, without excluding the sequencing reads that map to the first set of candidate alleles, if the sequencing reads that map to the locus, excluding the sequencing reads that map to the first set of candidate alleles, are greater than 1% of the number of sequencing reads that map to the first set of candidate alleles. In some embodiments, the third set of candidate alleles are only identified in if the number of sequencing reads that map to the alleles to which map the greatest number of sequencing reads, excluding the reads that map to the first or second set of candidate alleles, make up at least 10% of the total number of sequencing reads that map to the locus.

In some aspects, provided herein is a computer-implemented method of determining a genotype of a subject a locus of haploid DNA (e.g., a hypervariable region (HV) locus of mitochondrial DNA). In some embodiments, the method includes: a) receiving sequence data at a computer system, the sequence data comprising a plurality of sequencing reads; b) mapping, by the computer system, the sequencing reads to a reference sequence comprising a plurality of alleles of the locus to identify candidate alleles; and c) identifying, by the computer system, the one or more candidate alleles with the greatest likelihood of accounting for the sequencing reads that map to the locus as the allele that is present at the locus. In some embodiments, the alleles are HV alleles and the locus is a HV locus. In some embodiments, the alleles that are present at the locus make up the genotype at the locus. In some embodiments, the reference sequence also includes a genome sequence (e.g., a genome sequence with the locus masked or removed). In some embodiments the alleles and sequences are human. In some embodiments, the method includes the steps, performed by the computer system, of: i) mapping the sequencing reads to a reference sequence, the reference sequence comprising a human genome sequence and a plurality of allele sequences of the locus; ii) identifying as a first set of candidate alleles the alleles to which map the greatest number of sequencing reads; iii) identifying as a second set of candidate alleles the alleles to which map the greatest number of sequencing reads, excluding the sequencing reads that map to the first set of candidate alleles; and iv) if less than 90% of the sequencing reads that map to the locus map to an allele of the first or second set of candidate alleles, identifying as a third set of candidate alleles the alleles to which map the greatest number of sequencing reads, excluding the reads that map to the first or second set of candidate alleles. In some embodiments, the identified alleles are selected from a set of protein groups. In some embodiments, if the number of sequencing reads that map to the locus following exclusion of the sequencing reads that map to the first set of candidate alleles is greater than 1% of the number of sequencing reads that map to the first set of candidate alleles, further identifying as a subset of the second set of candidate alleles the alleles to which map the second greatest number of sequencing reads without excluding the sequencing reads that map to the first set of candidate alleles. In some embodiments the third set of candidate alleles are only identified in step iv) if the number of sequencing reads that map to the alleles to which map the greatest number of sequencing reads, excluding the reads that map to the first or second set of candidate alleles, make up at least 10% of the total number of sequencing reads that map to the locus.

In some embodiments, the one or more candidate alleles with the greatest likelihood of accounting for the sequencing reads are the one or more candidate alleles that have the greatest likelihood of accounting for: i) individual single nucleotide polymorphisms (SNPs) present in the sequencing reads that map to the candidate alleles; and ii) the sequential pairs of SNPs present in the sequencing reads that map to the candidate alleles.

In some embodiments, the one or more candidate alleles with the greatest likelihood of accounting for the sequencing reads are the one or more candidate alleles that have the greatest likelihood of accounting for: i) individual single nucleotide polymorphisms (SNPs) present in the sequencing reads that map to the candidate alleles; ii) the sequential pairs of SNPs present in the sequencing reads that map to the candidate alleles; and iii) the frequency of the pair of candidate alleles in humans. In some embodiments, the one or more candidate alleles with the greatest likelihood of accounting for the sequencing reads are determined by: i) for each individual candidate allele and each combination of candidate alleles, determining genotype log-likelihood scores for each individual SNP in the locus, each genotype log-likelihood score being the sum of the log-probabilities for each individual SNP in the locus individual candidate allele or combination of alleles could account for the sequences present at the individual SNP in the sequencing reads that map to the SNP; and ii) for each individual candidate allele and each combination of candidate alleles, determining phase log-likelihood scores for each sequential pair of SNPs in the locus, each phase log-likelihood score being the sum of the log-probabilities for each sequential pair of SNPs in the locus that the individual candidate allele or combination of candidate alleles could account for the sequences present at the sequential pair of SNPs in the sequencing reads that map to the sequential pair of SNPs; wherein the individual candidate allele or combination of candidate alleles for which the sum of the genotype log-likelihood scores and the phase log-likelihood scores is highest are the one or more candidate alleles with the greatest likelihood of accounting for the sequencing reads.

In some embodiments, the pair of candidate alleles with the greatest likelihood of accounting for the sequencing reads is determined by: i) for each individual candidate allele and each combination of candidate alleles, determining genotype log-likelihood scores for each individual SNP in the locus, each genotype log-likelihood score being the sum of the log-probabilities for each individual SNP in the locus individual candidate allele or combination of alleles could account for the sequences present at the individual SNP in the sequencing reads that map to the SNP; ii) for each individual candidate allele and each combination of candidate alleles, determining phase log-likelihood scores for each sequential pair of SNPs in the locus, each phase log-likelihood score being the sum of the log-probabilities for each sequential pair of SNPs in the locus that the individual candidate allele or combination of candidate alleles could account for the sequences present at the sequential pair of SNPs in the sequencing reads that map to the sequential pair of SNPs; and iii) for each individual candidate allele and each combination of candidate alleles, determining a frequency log-likelihood score, the frequency log-likelihood score being the sum of the log-frequencies at which each individual candidate allele and each combination of candidate alleles are present in the human population; wherein the individual candidate allele or combination of candidate alleles for which the sum of the genotype log-likelihood scores, the phase log-likelihood scores and the frequency log-likelihood score is highest are the one or more candidate alleles with the greatest likelihood of accounting for the sequencing reads.

In some aspects, provided herein is a method of transplanting an organ, tissue or cell to a subject, preventing transplant rejection and/or preventing graft versus host disease. In some embodiments, the method includes: a) obtaining sequence data of a subject, the sequence data comprising a plurality of sequencing reads; b) mapping the sequencing reads to a reference sequence comprising a plurality of HLA allele sequences of the HLA locus to identify candidate alleles; c) identifying the pair of candidate alleles with the greatest likelihood of accounting for the sequencing reads that map to the HLA locus as the alleles that make up the HLA type of the subject at the HLA locus; and d) transplanting to the subject an organ, tissue or cell having an HLA type at the HLA locus that matches the HLA type of the subject at the HLA locus. In some embodiments, the method includes: a) obtaining sequence data of an organ, tissue or cell, the sequence data comprising a plurality of sequencing reads; b) mapping the sequencing reads to a reference sequence comprising a plurality of HLA allele sequences of the HLA locus to identify candidate alleles; c) identifying the pair of candidate alleles with the greatest likelihood of accounting for the sequencing reads that map to the HLA locus as the alleles that make up the HLA type of the subject at the HLA locus; and d) transplanting the organ, tissue or cell to a subject having an HLA type at the HLA locus that matches the HLA type of the organ, tissue or cell at the HLA locus.

In some embodiments, step b) includes the steps of: i) mapping the sequencing reads to a reference sequence, the reference sequence comprising a human genome sequence and a plurality of HLA allele sequences of the HLA locus; ii) identifying as a first set of candidate alleles the HLA alleles to which map the greatest number of sequencing reads; iii) identifying as a second set of candidate alleles the HLA alleles to which map the greatest number of sequencing reads, excluding the sequencing reads that map to the first set of candidate alleles; and iv) if less than 90% of the sequencing reads that map to the HLA locus map to an allele of the first or second set of candidate alleles, identifying as a third set of candidate alleles the HLA alleles to which map the greatest number of sequencing reads, excluding the reads that map to the first or second set of candidate alleles. In some embodiments, the identified alleles are selected from a set of protein groups. In some embodiments, the third set of candidate alleles are only identified if the number of sequencing reads that map to the HLA alleles to which map the greatest number of sequencing reads, excluding the reads that map to the first or second set of candidate alleles, make up at least 10% of the total number of sequencing reads that map to the HLA locus.

In some embodiments, step b) includes the steps of: i) mapping the sequencing reads to a reference sequence at a low stringency, the reference sequence comprising a human genome sequence and a plurality of HLA allele sequences of the HLA locus; ii) identifying as pre-candidate alleles all alleles from each four-digit protein families for which at least one allele was among the top 10% of alleles mapped; iii) mapping the sequencing reads to a reference sequence at a higher stringency, the reference sequence comprising the pre-candidate alleles; iv) identifying as a first set of candidate alleles the pre-candidate alleles to which map the greatest number of sequencing reads; v) identifying as a second set of candidate alleles the pre-candidate alleles to which map the greatest number of sequencing reads, excluding the sequencing reads that map to the first set of candidate alleles; and vi) if less than 90% of the sequencing reads that map to the HLA locus map to an allele of the first or second set of candidate alleles, identifying as a third set of candidate alleles the pre-candidate alleles to which map the greatest number of sequencing reads, excluding the reads that map to the first or second set of candidate alleles. In some embodiments, the identified alleles are selected from a set of protein groups. In some embodiments, the third set of candidate alleles are only identified in if the number of sequencing reads that map to the HLA alleles to which map the greatest number of sequencing reads, excluding the reads that map to the first or second set of candidate alleles, make up at least 10% of the total number of sequencing reads that map to the HLA locus.

In some embodiments, the pair of candidate alleles with the greatest likelihood of accounting for the sequencing reads is the pair of candidate alleles that have the greatest likelihood of accounting for: i) individual single nucleotide polymorphisms (SNPs) present in the sequencing reads that map to the candidate alleles; and ii) the sequential pairs of SNPs present in the sequencing reads that map to the candidate alleles. In some embodiments, the pair of candidate alleles with the greatest likelihood of accounting for the sequencing reads is the pair of candidate alleles that have the greatest likelihood of accounting for: i) individual single nucleotide polymorphisms (SNPs) present in the sequencing reads that map to the candidate alleles; ii) the sequential pairs of SNPs present in the sequencing reads that map to the candidate alleles; and iii) the frequency of the pair of candidate alleles in humans.

In some embodiments, the pair of candidate alleles with the greatest likelihood of accounting for the sequencing reads is determined by: i) for each pair of candidate alleles, determining genotype log-likelihood scores for each individual SNP in the HLA locus, each genotype log-likelihood score being the sum of the log-probabilities for each individual SNP in the HLA locus that the pair of candidate alleles could account for the sequences present at the individual SNP in the sequencing reads that map to the SNP; and ii) for each pair of candidate alleles, determining phase log-likelihood scores for each sequential pair of SNPs in the HLA locus, each phase log-likelihood score being the sum of the log-probabilities for each sequential pair of SNPs in the HLA locus that the pair of candidate alleles could account for the sequences present at the sequential pair of SNPs in the sequencing reads that map to the sequential pair of SNPs, wherein the pair of candidate alleles for which the sum of the genotype log-likelihood scores and the phase log-likelihood scores is highest is the pair of candidate alleles with the greatest likelihood of accounting for the sequencing reads.

In some embodiments, the pair of candidate alleles with the greatest likelihood of accounting for the sequencing reads is determined by: i) for each pair of candidate alleles, determining genotype log-likelihood scores for each individual SNP in the HLA locus, each genotype log-likelihood score being the sum of the log-probabilities for each individual SNP in the HLA locus that the pair of candidate alleles could account for the sequences present at the individual SNP in the sequencing reads that map to the SNP; ii) for each pair of candidate alleles, determining phase log-likelihood scores for each sequential pair of SNPs in the HLA locus, each phase log-likelihood score being the sum of the log-probabilities for each sequential pair of SNPs in the HLA locus that the pair of candidate alleles could account for the sequences present at the sequential pair of SNPs in the sequencing reads that map to the sequential pair of SNPs; and iii) for each pair of candidate alleles, determining a frequency log-likelihood score, the frequency log-likelihood score being the sum of the log-frequencies at which each of the pair of candidate alleles are present in the human population, wherein the pair of candidate alleles for which the sum of the genotype log-likelihood scores, the phase log-likelihood scores and the frequency log-likelihood score is highest is the pair of candidate alleles with the greatest likelihood of accounting for the sequencing reads.

In some aspects, the method of transplanting an organ, tissue or cell to a subject, preventing transplant rejection and/or preventing graft versus host disease includes a) obtaining sequence data, of a subject the sequence data comprising a plurality of sequencing reads; b) mapping the sequencing reads to a reference sequence, the reference sequence comprising a human genome sequence and a plurality of HLA allele sequences of the HLA locus; c) identifying as a first set of candidate alleles the HLA alleles to which map the greatest number of sequencing reads; d) identifying as a second set of candidate alleles the HLA alleles to which map the greatest number of sequencing reads, excluding the sequencing reads that map to the first set of candidate alleles; e) if less than 90% of the sequencing reads that map to the HLA locus map to an allele of the first or second set of candidate alleles, identifying as a third set of candidate alleles the HLA alleles to which map the greatest number of sequencing reads excluding the reads that map to the first or second set of candidate alleles; f) for each pair of candidate alleles, determining genotype log-likelihood scores for each individual SNP in the HLA locus, each genotype log-likelihood score being the sum of the log-probabilities for each individual SNP in the HLA locus that the pair of candidate alleles could account for the sequences present at the individual SNP in the sequencing reads that map to the SNP; g) for each pair of candidate alleles, determining phase log-likelihood scores for each sequential pair of SNPs in the HLA locus, each phase log-likelihood score being the sum of the log-probabilities for each sequential pair of SNPs in the HLA locus that the pair of candidate alleles could account for the sequences present at the sequential pair of SNPs in the sequencing reads that map to the sequential pair of SNPs; h) for each pair of candidate alleles, determining a frequency log-likelihood score, the frequency log-likelihood score being the sum of the log-frequencies at which each of the pair of candidate alleles are present in the human population, wherein the HLA type of the subject at the HLA locus is the pair of candidate alleles for which the sum of the genotype log-likelihood scores, the phase log-likelihood scores and the frequency log-likelihood score is highest; i) transplanting to the subject an organ, tissue or cell having an HLA type at the HLA locus that matches the HLA type of the subject at the HLA locus. In some embodiments, the identified alleles are selected from a set of protein groups. In some embodiments, the third set of candidate alleles are only identified if the number of sequencing reads that map to the HLA alleles to which map the greatest number of sequencing reads, excluding the reads that map to the first or second set of candidate alleles, make up at least 10% of the total number of sequencing reads that map to the HLA locus.

In some embodiments, the method of transplanting an organ, tissue or cell to a subject, preventing transplant rejection and/or preventing graft versus host disease includes a) obtaining sequence data, of an organ, tissue or cell, the sequence data comprising a plurality of sequencing reads; b) mapping the sequencing reads to a reference sequence, the reference sequence comprising a human genome sequence and a plurality of HLA allele sequences of the HLA locus; c) identifying as a first set of candidate alleles the HLA alleles to which map the greatest number of sequencing reads; d) identifying as a second set of candidate alleles the HLA alleles to which map the greatest number of sequencing reads, excluding the sequencing reads that map to the first set of candidate alleles; e) if less than 90% of the sequencing reads that map to the HLA locus map to an allele of the first or second set of candidate alleles, identifying as a third set of candidate alleles the HLA alleles to which map the greatest number of sequencing reads excluding the reads that map to the first or second set of candidate alleles; f) for each pair of candidate alleles, determining genotype log-likelihood scores for each individual SNP in the HLA locus, each genotype log-likelihood score being the sum of the log-probabilities for each individual SNP in the HLA locus that the pair of candidate alleles could account for the sequences present at the individual SNP in the sequencing reads that map to the SNP; g) for each pair of candidate alleles, determining phase log-likelihood scores for each sequential pair of SNPs in the HLA locus, each phase log-likelihood score being the sum of the log-probabilities for each sequential pair of SNPs in the HLA locus that the pair of candidate alleles could account for the sequences present at the sequential pair of SNPs in the sequencing reads that map to the sequential pair of SNPs; h) for each pair of candidate alleles, determining a frequency log-likelihood score, the frequency log-likelihood score being the sum of the log-frequencies at which each of the pair of candidate alleles are present in the human population, wherein the HLA type of the subject at the HLA locus is the pair of candidate alleles for which the sum of the genotype log-likelihood scores, the phase log-likelihood scores and the frequency log-likelihood score is highest; i) transplanting the organ, tissue or cell to a subject having an HLA type at the HLA locus that matches the HLA type of the organ, tissue or cell at the HLA locus. In some embodiments, the identified alleles are selected from a set of protein groups. In some embodiments, the third set of candidate alleles are only identified if the number of sequencing reads that map to the HLA alleles to which map the greatest number of sequencing reads, excluding the reads that map to the first or second set of candidate alleles, make up at least 10% of the total number of sequencing reads that map to the HLA locus.

In some embodiments of the methods provided herein, the sequence data are genome-wide sequencing data. In some embodiments, the genome-wide sequencing data are transcriptome sequencing data, whole exome sequencing data or whole genome sequencing data. In some embodiments, the coverage of the sequence data is less than 60 fold, 50 fold, 40 fold, 30 fold, 20 fold or 15 fold. In some embodiments, the average length of the sequencing reads is less than 100, 90, 80, 70, 60, 50, 45, 40 or 35 nucleotides.

In certain embodiments of the methods provided herein, the reference sequence further comprises a human genome sequence. In some embodiments, the sequence of the HLA locus in the genome sequence has been removed or masked. In some embodiments, the human genome sequence is GRCh37/hg19.

In some embodiments, the methods described herein include the step of performing a genome-wide sequencing process on a sample to generate the sequence data. In some embodiments, the methods described herein include performing a nucleic acid amplification process that produces an amplification product that comprises a nucleic acid sequence of the HLA locus and performing a sequencing process on the amplification product.

In some embodiments of the methods provided herein, the organ, tissue or cell comprises skin, bone, a heart valve, a heart, a lung, a kidney, a liver, a pancreas, an intestine, a stomach, a testis or a portion thereof. In some embodiments, the organ, tissue or cell comprises bone marrow, hematopoietic stem cells or adult stem cells.

BRIEF DESCRIPTION OF THE DRAWINGS

FIG. 3 is a table showing the prediction accuracy of PHLAT, HLAminer, HLAforest, seq2HLA in HapMap RNAseq, 1000Genome WXS, HapMap WXS, and Targeted amplicon seq datasets. *The read alignment mode of HLAminer was applied for HapMap RNAseq dataset, and the contig assembly mode was applied for all other datasets. No p-value threshold was applied when calculating the accuracy of seq2HLA predictions in all datasets, which resulted in less false negatives (hence higher accuracies) than imposing a p-value cutoff of 0.1 as described earlier. #The value was reported in the text of an earlier publication.

FIG. 5 is a table providing the primers used in the targeted amplicon sequencing strategy used in Example 3 to generate the HLA sequence data for HLA typing. The sequences present in the table from top to bottom are SEQ ID NOs: 1-22, respectively.

DETAILED DESCRIPTION

General

Figure 1:
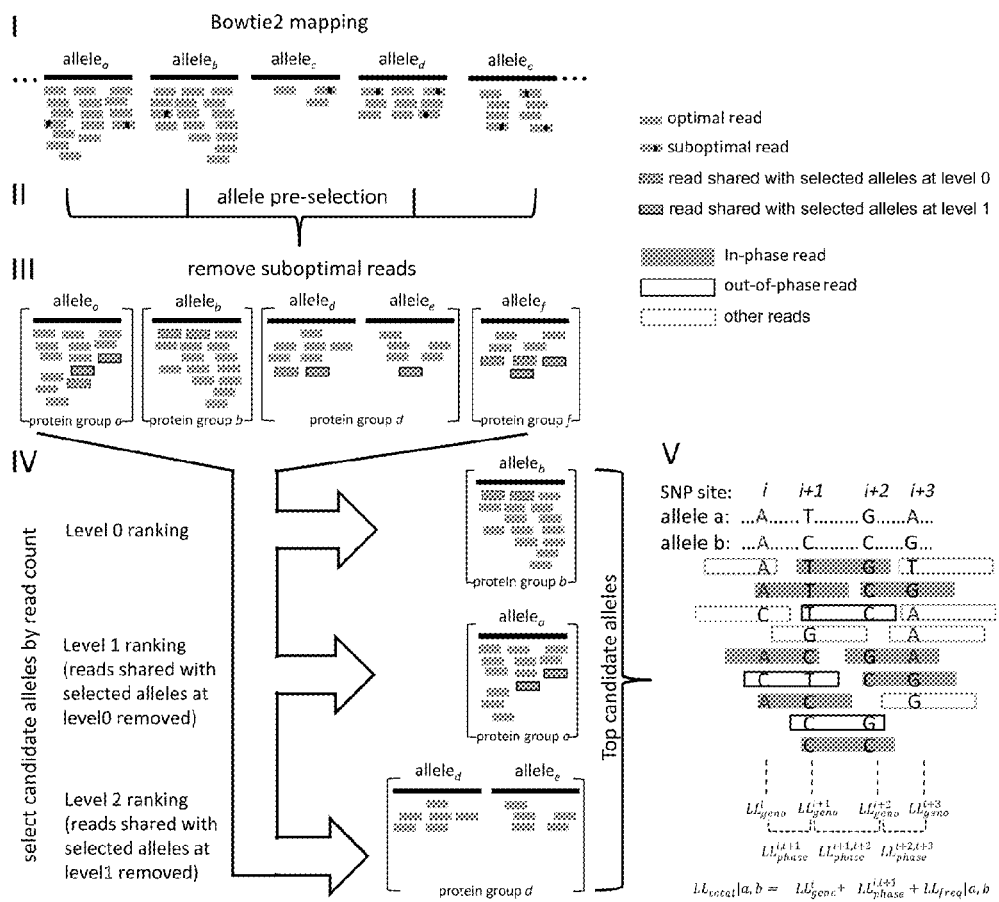
FIG. 1 is a workflow diagram illustrating an exemplary method in accordance with one or more embodiments. The method steps include read mapping via Bowtie 2 to the human genome with the HLA loci substituted by the genomic sequences of individual alleles (I), selection of top candidate alleles based on the number of mapped reads (II-IV), and log-likelihood scoring (V) over every pair of selected candidate alleles.

In certain aspects, provided herein is a process for accurately determining the alleles present at a locus (e.g., a highly polymorphic locus). In some embodiments, the method is referred to as PAT (Precise Allele lyping) or PHLAT (Precise HLA Typing). The terms PHLAT and PAT are used interchangeably herein. The PAT process is broadly applicable to the identification of the alleles present at any locus, including highly polymorphic loci such as HLA loci, BGA loci and HV loci. Certain embodiments of the PAT process are useful in a wide range of applications, including, for example, organ transplantation, personalized medicine, diagnostics, forensics and anthropology. For example, embodiments of the PAT process can be used to prevent organ rejection and graft versus host disease, to determine disease susceptibility, to optimize vaccination strategies, to predict therapeutic efficacy and to identify geographic and/ or ethnic origins.

In some embodiments, the PAT process is used to determine the HLA type at an HLA locus. The PAT process allows accurate four-digit and two-digit HLA typing using a wide range of sequencing data, even sequencing data that has short read lengths and/or low sequence coverage. Accurate HLA types can be predicted based on sequencing data generated using many different sequencing methods, including whole genome-wide sequencing methodologies (e.g., transcriptome sequencing, whole exome sequencing and whole genome sequencing) and HLA-specific sequencing methodologies (e.g., nucleic acid amplification of an HLA locus followed by sequencing of the resulting amplification product).

The PAT process can be used, for example, to facilitate transplantation of cells, organs or tissues between a donor and recipient having matching or partially matching HLA types. In some embodiments, the PAT process is used to identify and/or facilitate the treatment of individuals who are predisposed to certain diseases or conditions, including immunogenic diseases such as lupus, inflammatory bowel disease, multiple sclerosis, arthritis, type I diabetes, and cancer, such as breast or cervical cancer. In some embodiments, the PAT process is used to facilitate tumor immunotherapy and/or cancer vaccination therapies. In certain embodiments, the PAT process is used to determine the geographic and/or ethnic origin of a subject or sample.

In certain embodiments, the PAT process includes two parts: 1) the selection of candidate alleles from among the possible alleles of a locus; and 2) the ranking of pairs of the candidate alleles to identify which pair of candidate alleles is most likely to be the pair of alleles at the locus. In some embodiments, the candidate alleles are selected based on read counts. In some embodiments the pairs of candidate alleles are ranked based on the likelihood that observed data could be accounted for by each allele pair. In some embodiments, the most likely alleles are determined based on both the sequence consistency at individual positions and the phase consistency across consecutive positions. In some embodiments, the frequency of alleles in the human population is also factored into the ranking of the allele pairs. Flowcharts illustrating exemplary PAT processes in accordance with one or more embodiments are provided in FIGS. 7 and 8.

In some embodiments, the methods described herein can be used to determine the HLA type of any major or minor HLA locus. In some embodiments, the HLA locus is a class I HLA locus. In some embodiments, the HLA locus is an HLA-A locus, an HLA-B locus or an HLA-C locus. In some embodiments, the HLA locus is a class II HLA locus. In some embodiments, the HLA locus is an HLA-DQA1 locus, an HLA-DQB1 locus, an HLA-DRA locus, an HLA-DRB1 locus, an HLA-DRB3 locus, an HLA-DRB4 locus, an HLA-DRB5 locus, an HLA-DPA1 locus or an HLA-DPB1 locus. In some embodiments, the HLA locus is a minor HLA locus. The sequences of HLA alleles are known in the art. For example, genomic and coding DNA sequences (CDS) of HLA alleles can be obtained from IMGT release 3.8.0.

In some embodiments, the methods described herein are used to determine the genotype of a mitochondrial DNA locus, such as an HV locus (e.g., the hypervariable region 1 (HV1) locus or the hypervariable region 2 (HV2) locus). Unlike nuclear DNA, which is diploid and therefore has two copies of each locus, mitochondrial DNA is haploid, and therefore, in theory, would contain only one copy of the locus. However, loci in mitochondrial DNA are often duplicated. It is therefore possible for mitochondrial DNA to contain one, two or multiple copies of a loci. Thus, when the methods described herein are applied to mitochondrial DNA (or any locus encoded by a haploid genome, including germ-cell genomes, viral genomes or bacterial genomes) one or more alleles will be identified as being present at a locus, rather than a pair of alleles. The sequences of HV alleles are known in the art. HV allele sequences can be found, for example, in the HvrBase++ database (www.hvrbase.org), as described in Kohl et al., *Nucleic Acids Research* 34:D700-D704 (2006), hereby incorporated by reference in its entirety.

In some embodiments, the methods described herein are used to determine the alleles present at a BGA locus. Exemplary BGA loci include the ABO locus and the Rh locus. Sequences of BGA locus alleles are known in the art. For example, BGA locus sequences can be obtained from NCBI's Blood Group Antigen Gene Mutation Database (www.ncbi.nlm.nih.gov/projects/gv/rbc/xslcgi.fcgi?cmd=bgmut), as described in Patnaik et al., *Nucleic Acids Research* 40:D1023-D1029 (2012), hereby incorporated by reference in its entirety.

In certain embodiments, the processes described herein are computer-implemented. The processes may be implemented in software, hardware, firmware, or any combination thereof. The processes are preferably implemented in one or more computer programs executing on a programmable computer system including at least one processor, a storage medium readable by the processor (including, e.g., volatile and non-volatile memory and/or storage elements), and input and output devices. The computer system may comprise one or more physical machines or virtual machines running on one or more physical machines. In addition, the computer system may comprise a cluster of computers or numerous distributed computers that are connected by the Internet or other network.

Each computer program can be a set of instructions or program code in a code module resident in the random access memory of the computer system. Until required by the computer system, the set of instructions may be stored in another computer memory (e.g., in a hard disk drive, or in a removable memory such as an optical disk, external hard drive, memory card, or flash drive) or stored on another computer system and downloaded via the Internet or other network. Each computer program can be implemented in a variety of computer programming languages including, by way of example, Python.

Sequencing Data

Figure 7:
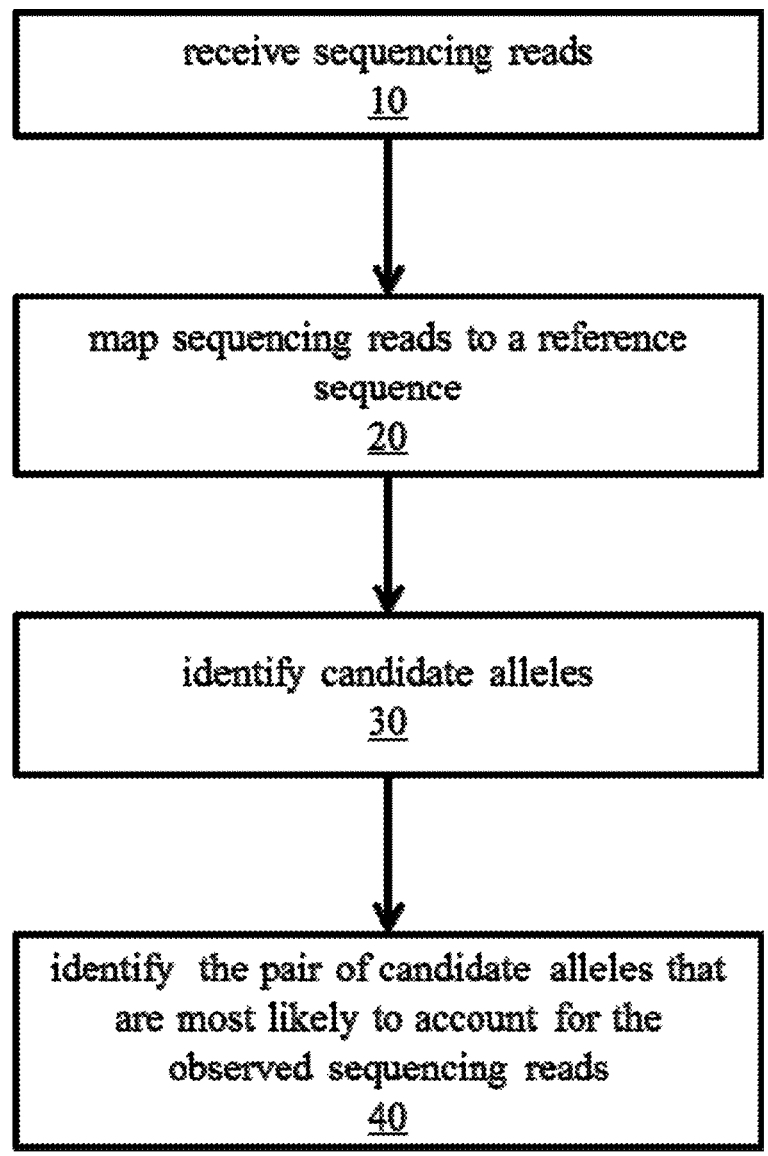
FIG. 7 is a flowchart illustrating an exemplary process in accordance with one or more embodiments.
Figure 8:
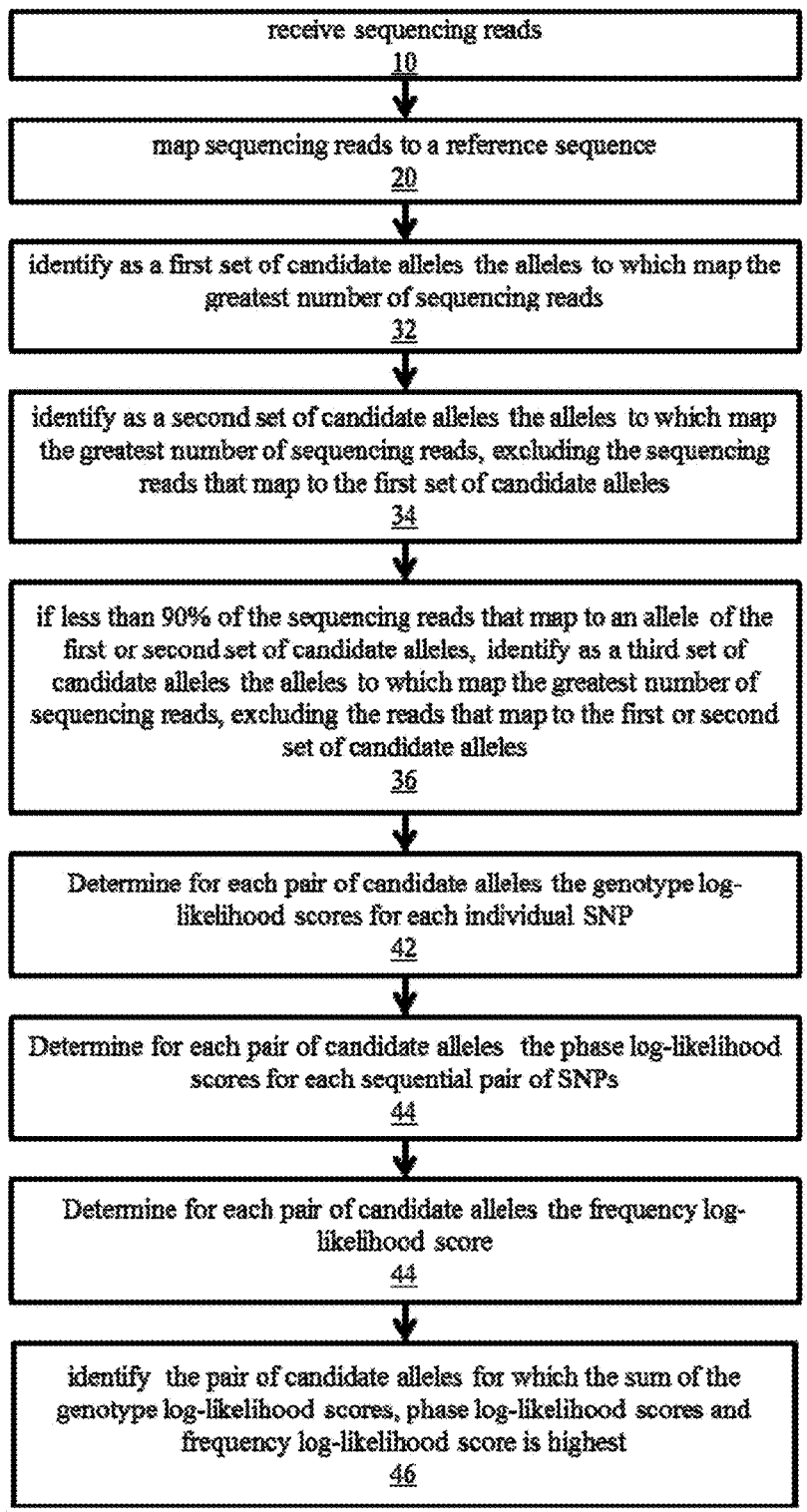
FIG. 8 is a flowchart illustrating an exemplary process in accordance with one or more embodiments.

In certain embodiments, the methods disclosed herein include the step of obtaining or receiving sequence data (e.g., step 10 of FIGS. 7 and 8). In some embodiments, sequence data can be obtained or received through any method. For example, the sequence data can be obtained directly, by performing a sequencing process on a sample. Alternatively, the sequence data can be obtained indirectly, for example, from a third party, a database and/or a publication. In some embodiments, the sequence data are received at a computer system, for example, from a data storage device or from a separate computer system.

The methods described herein are capable of accurately predicting the alleles present at a locus (e.g., the HLA type of a locus) using a wide range of sequence data. For example, in some embodiments, the sequence data are genome-wide sequencing data. In some embodiments, the sequence data are transcriptome sequencing data. In some embodiments, the sequence data are whole exome sequencing data. In some embodiments, the sequenced data are whole genome sequencing data. In some embodiments, the sequence data are enriched for sequence data encoding for the locus. In some embodiments, the sequence data are RNA sequence data. In some embodiments the sequence data are DNA sequence data.

In some embodiments, the sequence data comprise a plurality of sequencing reads. In some embodiments, the sequencing reads have an average read length of no more than 35, 36, 37, 38, 39, 40, 45, 50, 55, 60, 65, 70, 75, 80, 85, 90, 95, 100, 125, 150, 175, 200, 250, 300, 400, 500, 600, 700, 800, 900 or 1000 nucleotides. In some embodiments, the sequencing reads have an average read length of at least 30, 31, 32, 33, 34, 35, 36, 37, 38, 39, 40, 45, 50, 55, 60, 65, 70, 75, 80, 85, 90, 95, 100, 125, 150, 175, 200 or 250 nucleotides. In some embodiments the coverage of the sequencing reads is no more than 100×, 90×, 80×, 70×, 60×, 50×, 40×, 30× or 20×. In some embodiments the coverage of the sequencing reads is at least 50×, 45×, 40×, 35×, 30×, 25×, 20×, 19×, 18×, 17×, 16×, 15×, 14×, 13×, 12×, 11× or 10×.

In some embodiments, the sequence data can be produced by any sequencing method known in the art. For example, in some embodiments the sequencing data are produced using chain termination sequencing, sequencing by ligation, sequencing by synthesis, pyrosequencing, ion semiconductor sequencing, single-molecule real-time sequencing, dilute-'n'-go sequencing and/or 454 sequencing.

In some embodiments, the sequence data are the result of a process whereby a nucleic acid amplification process is performed to amplify at least part of one or more genomic locus or transcript, followed by the sequencing of the resulting amplification product. Examples of nucleic acid amplification processes useful in the performance of methods disclosed herein include, but are not limited to, polymerase chain reaction (PCR), LATE-PCR, ligase chain reaction (LCR), strand displacement amplification (SDA), transcription mediated amplification (TMA), self-sustained sequence replication (3SR), Qβ replicase based amplification, nucleic acid sequence-based amplification (NASBA), repair chain reaction (RCR), boomerang DNA amplification (BDA) and/or rolling circle amplification (RCA).

In some embodiments, the method includes the step of performing a sequencing process on a sample. Any sample can be used, so long as the sample contains DNA and/or RNA (e.g., DNA or RNA encoding an HLA molecule). In some embodiments, the sample is from a perspective organ, cell or tissue donor. In some embodiments, the sample is from a perspective organ, cell or tissue recipient. The source of the sample may be, for example, solid tissue, as from a fresh, frozen and/or preserved organ, tissue sample, biopsy, or aspirate; blood or any blood constituents, serum, blood; bodily fluids such as cerebral spinal fluid, amniotic fluid, peritoneal fluid or interstitial fluid, urine, saliva, stool, tears; or cells from any time in gestation or development of the subject.

In some embodiments, any sequencing method available in the art is performed. In some embodiments the sequencing is performed using chain termination sequencing, sequencing by ligation, sequencing by synthesis, pyrosequencing, ion semiconductor sequencing, single-molecule real-time sequencing, dilute-'n'-go sequencing and/or 454 sequencing. In some embodiments, a nucleic acid amplification process is performed to amplify at least part of one or more genomic locus or transcript (e.g., an HLA genomic locus or transcript), followed by the sequencing of the resulting amplification product. In some embodiments, the nucleic acid amplification method performed is polymerase chain reaction (PCR), LATE-PCR, ligase chain reaction (LCR), strand displacement amplification (SDA), transcription mediated amplification (TMA), self-sustained sequence replication (3SR), Qβ replicase based amplification, nucleic acid sequence-based amplification (NASBA), repair chain reaction (RCR), boomerang DNA amplification (BDA) and/or rolling circle amplification (RCA).

Selection of Candidate Alleles

In some embodiments, the methods disclosed herein include a step for the selection of candidate alleles (e.g., steps 20 and 30 of FIG. 7 and steps 20, 32, 34 and 36 of FIG. 8). In some embodiments, the selection of candidate alleles is performed by mapping sequencing reads to a reference sequence, followed by a series of read counting steps. This mapping process can be performed, for example, using any available sequence mapping software. In certain embodiments, Bowtie 2 is used. In some embodiments, the Bowtie 2 mapping parameter is set as very-sensitive (i.e. —D 20—R 3—N 0—L 20—I 5, 1, 0.50) in the end-to-end mode. In some embodiments, the reference sequence includes a plurality of alleles, such as HLA alleles (e.g., on artificial chromosomes). In some embodiments, the reference sequence further includes a human genome sequence (e.g., GRCh37/hg19). In some embodiments, one or more locus (e.g., an HLA locus) in the human genome sequence are excluded from the reference sequence or masked (e.g., by replacing the locus sequence with Ns).

The alleles included in the reference sequence can be obtained from any source of allele sequences. For example, if HLA alleles are included in the reference sequence, genomic and coding DNA sequences (CDS) of the alleles can be obtained from IMGT release 3.8.0 and mapped to the coordinates in human reference genome build 37/hg19. In some embodiments, only the genomic sequences of the alleles from transcription start site to the stop codon are included in the reference sequence. Alleles with only CDS but not genomic record can be used by filling in the non-coding regions with the genomic sequence of a reference allele (e.g., the sequence from the hg19 genome at the corresponding locus). Without being bound by theory, the genomic sequence imputation of non-coding sequences has little or no impact on HLA typing because polymorphisms in non-coding regions do not alter HLA types at the protein level.

In some embodiments, prior to the selection of candidate alleles, pre-candidate alleles are selected by mapping the sequence reads to the reference sequence at a low stringency. In some embodiments, an upper quantile threshold (e.g. the upper 95th, 90th, 85th, 80th, 75th, 70th, 65th, 60th, 55th or 50th percentile) of the read counts was applied for a coarse pre-selection of possible alleles. In some embodiments, the upper quantile threshold is the upper 90th percentile. In some embodiments, the upper quantile threshold is 70th percentile. In some embodiments, the upper quantile is the upper 90th percentile if there are a large number of alleles at a locus (e.g., at least 200, 300, 400, 500, 600, 700, 800, 900 or 1000 alleles) but the upper quantile threshold is the upper 70th percentile if a small number of alleles are present at a locus (e.g., no more than 200, 300, 400, 500, 600, 700, 800, 900 or 1000 alleles). In some embodiments, all alleles from a protein (four-digit) family are retained so long as at least one member of the family fell within the threshold. In certain embodiments, all alleles from each four-digit protein families for which at least one allele is among the top 5%, 10%, 15%, 20%, 25% or 30% of alleles mapped are selected as pre-candidate alleles. In some embodiments, the top 10% of alleles mapped are selected. In some embodiments, the top 30% of alleles mapped are selected. In some embodiments, the top 10% of alleles mapped are selected if there are a large number of alleles at a locus (e.g., at least 200, 300, 400, 500, 600, 700, 800, 900 or 1000 alleles) but the top 30% of alleles mapped are selected if a small number of alleles are present at a locus (e.g., no more than 200, 300, 400, 500, 600, 700, 800, 900 or 1000 alleles). In some embodiments, only pre-candidate alleles are included in the subsequent candidate selection process. In some embodiments, all alleles in the reference sequence are included in the subsequent candidate selection process. An exemplary embodiment of this pre-selection process is illustrated in steps I and II of FIG. 1.

In some embodiments, the number of reads mapped to the retained alleles are calculated using a stringent criterion. For example, in some embodiments reads are only counted for the allele it matches best (or multiple alleles if tied) judging by the sequence identity over SNP sites within the corresponding locus that were covered by the read. In some embodiments, at least 99% sequence identity is required to count a read. In some embodiments, the SNPs per locus are the polymorphic sites of the retained alleles at that locus. In some embodiments, sites that coincide with indels (insertions or deletions) in any of the retained alleles are excluded. An exemplary embodiment of this mapping process is illustrated in step III of FIG. 1.

In certain embodiments, candidate alleles are selected using a series of read-counting steps (e.g., steps 32, 34 and 36 of FIG. 8). In some embodiments, the alleles to which map the greatest number of sequencing reads are identified as a first set of candidate alleles. In some embodiments, the alleles to which map the greatest number of sequencing reads, excluding the sequencing reads that map to the first set of candidate alleles, are identified as a second set of candidate alleles. In some embodiments, if less than 95%, 90%, 85% or 80% of the sequencing reads that map to the locus map to an allele of the first or second set of candidate alleles, the alleles to which map the greatest number of sequencing reads, excluding the reads that map to the first or second set of candidate alleles, are identified as a third set of candidate alleles. In some embodiments, the identified alleles are selected from a set of protein groups.

An exemplary embodiment of the candidate allele selection process is illustrated in step IV of FIG. 1. In this embodiment, the alleles are first sorted by read counts from high to low, (referred to as level 0 ranking in FIG. 1). The allele (or alleles if tied) with the largest read counts is selected and stored as candidates. Then the read counts in the remaining alleles are adjusted by excluding the reads shared with the previously selected alleles. The adjusted read counts are sorted in descending order (referred to as level 1 ranking in FIG. 1) and the new top allele (or alleles if tied) is selected as a candidate allele. To tolerate uncertainties in read mapping and counting, the alleles from the second top ranking alleles at level 0 are included as candidate alleles if they possessed a non-negligible number of reads distinct from the top alleles. For example, in some embodiments the alleles to which the second greatest number of sequencing reads map before excluding the sequencing reads that map to the first set of candidate alleles are included in the level 1 ranking if, after exclusion of the reads that map to alleles selected in the level 0 ranking, they retain a number of sequencing reads that is at least 1% of the number of sequencing reads mapped to level 0 ranked alleles. If the alleles selected from level 0 and level 1 rankings account for less than 90% of the alleles mapped to the locus, the read counting procedure is repeated (referred to as level 2 ranking in FIG. 1) and the new top allele (or alleles if tied) is included among the candidate alleles if at least 10% of the sequencing reads that map to the locus map to new top allele or alleles.

In some embodiments, the locus is determined to be homozygous (i.e., both copies of the locus contain the same allele) if the following criteria are satisfied: the top allele in level 0 accounted for at least 80%, 85%, 90% or 95% of the reads and no other allele accounted for more than 3%, 4%, 5%, 6%, 7%, 8%, 9% or 10% of the remaining reads. In some embodiments, the locus is determined to be homozygous if the following criteria are satisfied: the top allele in level 0 accounted for at least 90% of the reads that mapped to the locus, and no other allele accounted for, excluding the reads mapped to the top allele in level 0, more than 5% of the reads that mapped to the locus.

Likelihood Ranking

In certain embodiments, following performance of the above candidate selection process, only candidate alleles and their associated reads are included in subsequent analysis. In some embodiments, the candidate alleles are subjected to evaluation over all pair-wise combinations (including self-pair) of the candidate alleles to discover the pair that is most likely to be present at the locus (e.g., the pair most likely to make up the HLA type). Examples of this aspect of the process are depicted in step 40 of FIG. 7 and steps 42, 44 and 46 of FIG. 8.

In some embodiments, the methods provided herein include steps for identifying a pair of candidate alleles that have the greatest likelihood of being the alleles present at a locus. In some embodiments, the pair of candidate alleles identified are the pair with the greatest likelihood of accounting for the sequences of the sequencing reads that map to the locus. In some embodiments, the pair of candidate alleles identified are the pair that have the greatest likelihood of accounting for: 1) individual single nucleotide polymorphisms (SNPs) present in the sequencing reads that map to the candidate alleles; and 2) the sequential pairs of SNPs present in the sequencing reads that map to the candidate alleles. In some embodiments, the pair of candidate alleles identified are the pair that have the greatest likelihood of accounting for: 1) individual single nucleotide polymorphisms (SNPs) present in the sequencing reads that map to the candidate alleles; 2) the sequential pairs of SNPs present in the sequencing reads that map to the candidate alleles; and 3) the frequency of the pair of candidate alleles in humans.

In some embodiments, the pair of candidate alleles with the greatest likelihood of accounting for the sequences of the sequencing reads that map to the candidate alleles are determined by: 1) for each pair of candidate alleles, determining genotype log-likelihood scores for each individual SNP in the locus, each genotype log-likelihood score being the sum of the log-probabilities for each individual SNP in the locus that the pair of candidate alleles could account for the sequences present at the individual SNP in the sequencing reads that map to the SNP; and 2) for each pair of candidate alleles, determining phase log-likelihood scores for each sequential pair of SNPs in the locus, each phase log-likelihood score being the sum of the log-probabilities for each sequential pair of SNPs in the locus that the pair of candidate alleles could account for the sequences present at the sequential pair of SNPs in the sequencing reads that map to the sequential pair of SNPs; wherein the pair of candidate alleles for which the sum of the genotype log-likelihood scores and the phase log-likelihood scores is highest is the pair of candidate alleles with the greatest likelihood of accounting for the sequencing reads.

In some embodiments, the pair of candidate alleles with the greatest likelihood of accounting for the sequences of the sequencing reads that map to the candidate alleles are determined by: 1) for each pair of candidate alleles, determining genotype log-likelihood scores for each individual SNP in the locus, each genotype log-likelihood score being the sum of the log-probabilities for each individual SNP in the locus that the pair of candidate alleles could account for the sequences present at the individual SNP in the sequencing reads that map to the SNP; 2) for each pair of candidate alleles, determining phase log-likelihood scores for each sequential pair of SNPs in the locus, each phase log-likelihood score being the sum of the log-probabilities for each sequential pair of SNPs in the locus that the pair of candidate alleles could account for the sequences present at the sequential pair of SNPs in the sequencing reads that map to the sequential pair of SNPs; and 3) for each pair of candidate alleles, determining a frequency log-likelihood score, the frequency log-likelihood score being the sum of the log-frequencies at which each of the pair of candidate alleles are present in the human population; wherein the pair of candidate alleles for which the sum of the genotype log-likelihood scores, the phase log-likelihood scores and the frequency log-likelihood score is highest is the pair of candidate alleles with the greatest likelihood of accounting for the sequencing reads.

In some embodiments, the pair of candidate alleles with the highest log-likelihood score ($^{LL}$total) is identified as the alleles present at the locus (e.g., the HLA type at the HLA locus). In some embodiments, the $^{LL}$total is calculated according to eq. 1. As shown in eq. 1, ($^{LL}$total) of each allele pair integrates the likelihoods of the observed genotype over individual SNP sites ($^{LL}$geno) and the phase across multiple sites ($^{LL}$phase), together with the probability of the allele pair present in human ($^{LL}$freq).

$$LL_{total} = \Sigma LL_{geno}{}^{i} + \Sigma LL_{phase}{}^{i,i+1} + LL_{freq}{}^{i}, i \in SNP \text{ Sites at a given locus} \quad \text{(eq. 1)}$$

Genotype Likelihood Scoring

In some embodiments, the log-likelihood score for an individual SNP in a locus ($^{LL}$geno) is calculated according to a Bayesian model. In some embodiments, the posterior log-likelihood ($LL_{gene}{}^{i}$) is proportional to the conditional log-likelihood log $P(D^i|G^i)$, which is the log-probability of observing the piled up bases ($D^i$) given the genotype of the allele pair interested ($G^i$) at site i. The marginal prior log $P(G^i)$ is assumed constant for any genotype and therefore removed. $P(D^i|G^i)$ is the product of individual conditional log-likelihoods of observing a base j at site i, $P(b_j{}^i|G^i)$(eq. 2).

$$P(D^i \mid G^i) = \prod_j P(b^i_j \mid G^i), \quad \text{(eq. 2)}$$

$b^i_j$ = base of read $j$ at site $i$, $G^i = g^i_1 g^i_2$ $P(b^i_j \mid Gi) = 1 - q_j$ $$= \frac{1-q_j}{2} + \frac{q_j/3}{2}$$

$$= g_j/3$$

$g^i_1 = g^i_2 = b^i_j$ $g^i_1 \neq g^i_2$ and $b^i_j = g^i_1$ or $b^i_j = g^i_2$ $b^i_j \neq g^i_1$ and $b^i_j \neq g^i_2$ $q_1$ is the error rate converted from the Phred score of the base j.

Phase Likelihood Scoring

In some embodiments, the phase likelihood over two adjacent SNP sites ($^{LL}$phase) is modeled analogously to the genotype likelihood of one SNP site, described above. $LL_{phase}{}^{i,i+1}$ is proportional to the log-probability of observing the pairs of bases on the same strand across two adjacent SNP sites i and i+1 ($D^i$), given the phase sequence of the allele pair interested at the two sites ($G^{i,i+1}$). There are 15 possible mismatch (out-of-phase) states and 1 matching (in-phase) state across two sites. $P(D^{i,i+1}|H^{i,i+1})$ is the product of the conditional log-likelihoods from all reads covering the site i and i+1 (eq. 3). $q_{err}$ is the out-of-phase error rate (0.01).

$$P(D^{i,i+1} \mid G^{i,i+1}) = \prod_j P(r_j^{i,i+1} \mid G^{i,i+1}) \qquad (eq.\ 3)$$

$r_j^{i,i+1} = b_j^i b_j^{i+1}$, the pair of base on read $j$ at site $i$ and $i+1$ $G^{i,i+1} = (g_1^i g_1^{i+1},\ g_2^i g_2^{i+1})$, $\quad g_1^i g_1^{i+1}$ and $g_2^i g_2^{i+1}$ for allele 1 and 2, respectively $P(r_j^{i,i+1} \mid G^{i,i+1}) = 1 - q_{err}$ $g_1^i g_1^{i+1} = g_2^i g_2^{i+1} = b_j^i b_j^{i+1} = \dfrac{1 - q_{err}}{2} + \dfrac{q_{err}/15}{2}$ $g_1^i g_1^{i+1} \neq g_2^i g_2^{i+1}$, $b_j^i b_j^{i+1} = g_1^i g_1^{i+1}$ or $b_j^i b_j^{i+1} = g_2^i g_2^{i+1} = q_{err}/15$ $b_j^i b_j^{i+1} \neq g_1^i g_1^{i+1}$ and $b_j^i b_j^{i+1} \neq g_2^i g_2^{i+1}$ Eq. 3 avoids the bias of favoring allele pairs with heterogeneous phase sequence ($g_1^i g_1^{i+1}$, $g_2^i g_2^{i+1}$), $g_1^i g_1^{i+1} \approx g_2^i g_2^{i+1}$ induced by calculating a binomial probability based on the number of in-phase and out-of-phase reads. The in-phase read count for the heterogeneous phase is the sum of, and therefore always larger than, the in-phase read. The counts supporting the two homogeneous phases ($g_1^i g_1^{i+1}$, $g_1^i g_1^{i+1}$) and ($g_2^i g_2^{i+1}$, $g_2^i g_2^{i+1}$). Thus, the heterogeneous phase always has a higher probability than the two corresponding homogeneous phases in the binomial model. In contrast, the Bayesian model described herein favors a heterogeneous phase only with roughly balanced $g_1^i g_1^{i+1}$ and $g_2^i g_2^{i+1}$ reads but not when one type predominates, which suggests a homogeneous phase after all.

Allele Frequency Scoring

In some embodiments, the log-frequencies at which each of the pair of candidate alleles are present in the human population are considered when determining the most likely pair of candidate alleles. Allele frequencies for the major class I and II loci are known in the art. For example, such allele frequencies can be downloaded from Allele Frequency Net. In some embodiments, for each protein (four-digit) family, the maximum frequency from the documented alleles was used and shared by all the alleles within. In some embodiments, a background value of 0.0001 is assigned to any protein family (and its alleles) with unknown frequency. In some embodiments, $^{LL}$freq is computed as the sum of the log-frequencies of the two alleles.

Transplantation Methods

In some aspects, the HLA typing methods described herein can be used to reduce the likelihood of transplantation rejection and/or graft versus host disease. In some certain aspects, provided herein are methods of performing an organ, cell or tissue transplantation. In some embodiments, the transplantation methods include performing an HLA typing method described herein to determine the HLA type of an organ, tissue or cell of at least one HLA locus, and then transplanting the organ, tissue or cell to a recipient. In some embodiments, the transplantation methods include performing an HLA typing method described herein to determine the HLA type of a perspective transplantation recipient at at least one HLA locus, and then transplanting an organ, tissue or cell to the recipient. In some embodiments, the transplantation methods include performing an HLA typing method described herein to determine the HLA type of an organ, tissue or cell at of least one HLA locus, performing an HLA typing method described herein to determine the HLA type of a perspective transplantation recipient of at least one HLA locus and then transplanting the organ, tissue or cell to the recipient.

In some certain aspects, provided herein are methods of preventing rejection of a transplanted organ, tissue or cell. In some embodiments, the methods include performing an HLA typing method described herein to determine the HLA type of an organ, tissue or cell of at least one HLA locus, and then transplanting the organ, tissue or cell of to a recipient. In some embodiments, the methods include performing an HLA typing method described herein to determine the HLA type of a perspective transplantation recipient of at least one HLA locus, and then transplanting an organ, tissue or cell to the recipient. In some embodiments, the methods include performing an HLA typing method described herein to determine the HLA type of an organ, tissue or cell at of least one HLA locus, performing an HLA typing method described herein to determine the HLA type of a perspective transplantation recipient at at least one HLA locus and then transplanting the organ, tissue or cell to the recipient.

In some certain aspects, provided herein are methods of preventing graft versus host disease. In some embodiments, the methods include performing an HLA typing method described herein to determine the HLA type of an organ, tissue or cell of at least one HLA locus, and then transplanting the organ, tissue or cell to a recipient. In some embodiments, the methods include performing an HLA typing method described herein to determine the HLA type of a perspective transplantation recipient of at least one HLA locus, and then transplanting an organ, tissue or cell to the recipient. In some embodiments, the methods include performing an HLA typing method described herein to determine the HLA type of an organ, tissue or cell of at least one HLA locus, performing an HLA typing method described herein to determine the HLA type of a perspective transplantation recipient at at least one HLA locus and then transplanting the organ, tissue or cell to the recipient. In some embodiments, the HLA type is determined at 2 digit resolution. In some embodiments, the HLA type is determined at 4 digit resolution.

In some embodiments, the HLA locus tested prior to transplantation is a class I HLA locus. In some embodiments, the HLA locus is an HLA-A locus, an HLA-B locus or an HLA-C locus. In some embodiments, the HLA locus is a class II HLA locus. In some embodiments, the HLA locus is an HLA-DQA1 locus, an HLA-DQB1 locus, an HLA-DRA locus, an HLA-DRB1 locus, an HLA-DRB3 locus, an HLA-DRB4 locus, an HLA-DRBS locus, an HLA-DPA1 locus or an HLA-DPB1 locus. In some embodiments, the HLA type is determined for multiple HLA loci. For example, in some embodiments, the HLA type is determined for at least 2, 3, 4, 5, 6, 7, 8, 9, 10, 11 or 12 HLA loci. In some embodiments, the HLA type is determined for all three of the class I HLA loci (HLA-A, HLA-B and HLA-C). In some embodiments, the HLA type is determined for HLA-A, HLA-B, HLA-C, HLA-DQA1, HLA-DQB1 and HLA-DRB1. In some embodiments, the HLA type is determined for HLA-A, HLA-B and HLA-DRB1.

In some embodiments, the HLA type of the organ, tissue or cell matches the HLA type of the recipient at the HLA locus. In some embodiments, the HLA locus is an HLA-A locus, an HLA-B locus or an HLA-C locus. In some embodiments, the HLA locus is an HLA-DQA1 locus, an HLA-DQB1 locus, an HLA-DRA locus, an HLA-DRB1 locus, an HLA-DRB3 locus, an HLA-DRB4 locus, an HLA-DRBS locus, an HLA-DPA1 locus or an HLA-DPB1 locus. In some embodiments, the HLA type of the organ, tissue or cell matches the HLA type of the recipient of at least 2, 3, 4, 5, 6, 7, 8, 9, 10, 11 or 12 HLA loci. In some embodiments, the HLA type of the organ, tissue or cell matches the HLA type of the recipient of at least 2 class I HLA loci. In some embodiments, the HLA type of the organ, tissue or cell matches the HLA type of the recipient at all three class I HLA loci. In some embodiments, the HLA type of the organ, tissue or cell matches the HLA type of the recipient at the HLA-A locus and the HLA-B locus. In some embodiments, the HLA type of the organ, tissue or cell matches the HLA type of the recipient at the HLA-A locus, the HLA-B locus and the HLA-DRB1 locus. In some embodiments, the HLA type of the organ, tissue or cell does not match the HLA type of the recipient at no more than 11, 10, 9, 8, 7, 6, 5, 4, 3, 2 or 1 HLA loci. In some embodiments, the match is at 2 digit resolution. In some embodiments the match is at four-digit resolution.

In some embodiments of the methods provided herein, an organ is transplanted. In some embodiments, the organ transplanted is a heart, a lung, a kidney, a liver, a pancreas, an intestine, a stomach and/or a testis or a portion of one of the foregoing organs. In some embodiments, the transplanted cell, tissue or organ is a limb (e.g., a hand, foot, arm or leg), a cornea, skin, a face, islets of Langerhans, bone marrow, hematopoietic stem cells, adult stem cells (e.g., mammary stem cells, intestinal stem cells, mesenchymal stem cells, endothelial stem cells, neural stem cells, olfactory stem cells, cardiac stem cells, lung stem cells), a blood vessel, a heart valve and/or a bone. The transplanted organ, tissue or cell can be from a living donor or a deceased donor.

In some embodiments of the methods provided herein, the recipient of the organ, tissue or cell is administered an agent that reduces the likelihood of transplant rejection. In some embodiments, the agent is an immunosuppressive agent. In certain embodiments, the recipient is administered prednistolone, hydrocortisone, ciclosporin, tacrolimus, azathioprine, mycophenolic acid, sirolimus, everolimus, basiliximab, daclizumab, anti-thymocyte globulin, anti-lymphocyte globulin, and/or rituximab. In some embodiments, the recipient is administered the agent if the HLA type of the recipient does not match the HLA type of the transplanted organ, cell or tissue at one or more HLA loci. In some embodiments, the recipient is administered the agent if the HLA type of the recipient does not match the HLA type of the transplanted organ, cell or tissue at at least 1, 2, 3, 4, 5, 6, 7, 8, 9, 10 or 11 HLA loci.

All publications, including patents, applications, and GenBank Accession numbers mentioned herein are hereby incorporated by reference in their entirety as if each individual publication or patent was specifically and individually indicated to be incorporated by reference. In case of conflict, the present application, including any definitions herein, will control.

The invention now being generally described, it will be more readily understood by reference to the following examples, which are included merely for purposes of illustration of certain aspects and embodiments of the present invention, and are not intended to limit the invention.

EXEMPLIFICATION

Example 1

HLA Typing using an Embodiment of the PHLAT Process

The PHLAT workflow started with a reference-based read mapping (step I in FIG. 1) using Bowtie 2. The reference genome was constructed by extending human genome GRCh37/hg19 with a collection of artificial chromosomes, each of which presented the genomic DNA sequence of one HLA allele. The corresponding genomic sequences at HLA-A, B, C, DQA1, DQB1 and DRB1 loci on the chromosome 6 were masked by N's to avoid duplicated mapping. The Bowtie 2 mapping parameter was set as —very-sensitive (i.e. —D 20 —R 3 —N 0 —L 20 —I 5,1,0.50) in the —end-to-end mode. The best alignment (or one of the equally good alignments) for each read was reported. Performance of PHLAT did not alter significantly by changing the mapping engine to Bowtie when the read lengths were applicable to it (data not shown).

A total of 7059 alleles for major class I and II loci HLA-A (1884), HLA-B (2489), HLA-C (1382), HLA-DQA1 (47), HLA-DQB1 (165) and HLA-DRB1 (1092) were included in the reference sequence. The genomic and coding DNA sequences (CDS) of the alleles were obtained from IMGT release 3.8.0 and mapped to the coordinates in human reference genome build 37/hg19. The genomic DNA sequences were used for Bowtie 2 mapping (FIG. 1, step I and see below) whereas CDS sequences were used for all other procedures (FIG. 1 steps II-V). Only the genomic sequences from transcription start site (TSS) to the stop codon were retained. For any allele with only CDS but not a genomic record, the non-coding regions were filled with the genomic sequence of the reference allele used in the hg19 genome at the corresponding locus (e.g. A*03:01:01:01 is the reference allele for HLA-A locus), so long as no available data had suggested variations outside the CDS regions of that allele. The genomic sequence imputation had little if any impact to HLA typing, as polymorphisms in non-coding regions did not alter HLA types at the protein level.

The following HLA type predictions were accomplished in two major steps: a selection of top candidate alleles (step II-IV in FIG. 1) and a likelihood based ranking (step V in FIG. 1). The allele selection greatly reduced the computational cost of the likelihood ranking during which every pair-wise combination of alleles must be evaluated. Subsequently, the likelihood scores integrated genotype and phase information as well as prior knowledge to resolve the highly homologous HLA alleles at high resolution.

The top candidate allele selection involved iterations of read counting. First, upon the Bowtie 2 mapping results, the number of reads mapped to each allele was counted. An upper quantile threshold (e.g. 90 percentile) of the read counts was applied for a coarse pre-selection of possible alleles (step II in FIG. 1). All alleles from one peptide (four-digit) family were retained as long as one member of the family was selected. Next, the number of reads mapped to the retained alleles was recomputed according to a more stringent criterion (step III in FIG. 1). Using the coordinate of each read output by Bowtie 2, the read was compared against all retained alleles at this location. Only the read for the allele it matched best (or multiple alleles if tied) was counted, judging by the sequence identity over the SNP sites within the corresponding locus that were covered by this read. At least 99% sequence identity was required to count a read at all. The SNPs per locus were the union of the polymorphic sites from the retained alleles at that locus. The sites that coincided with indels in any of the kept alleles were excluded to avoid alignment bias, as indels were not considered as mismatches. The read counts were summarized non-redundantly per protein group (four-digit) and used for top candidate allele selection via sequential count-based rankings (step IV in FIG. 1). Specifically, for a given locus, the protein groups were first sorted by read counts from high to low, referred as level 0 ranking. The group (or groups if tied) with the largest read counts were selected and all associated alleles were stored as candidates. Then the read counts in the remaining protein groups were adjusted by excluding the reads shared with the previously selected groups. The adjusted read counts were sorted in descending order (level 1 ranking) and the new top groups were selected. To tolerate uncertainties in read mapping and counting, especially when the sequencing coverage was limited or the true and false alleles were much alike, the alleles from the second top ranking protein groups at level 0 were included if they possessed a non-negligible number of unique reads (>1% of the reads mapped to the top ranking group) that are not shared with the top groups. Often the alleles selected from level 0 and level 1 rankings could explain the majority of the reads (>=90%) mapped to the locus. Otherwise, the procedure was repeated (level 2 ranking) and the new top protein group at the locus were selected.

A homozygous genotype at four-digit resolution might be determined at this candidate allele selection step if the following criteria were satisfied: the top protein group in level 0 explained the majority of the reads (>90%) and the remaining reads explained by any other groups were negligible (less than 5%) compared to the explained ones.

At the end of the selection, only the candidate alleles and their associated reads were used for subsequent analysis. Typically, a few tens of alleles remained. This number was small enough for an exhaustive evaluation over all pair-wise combinations (including self-pair) of the alleles to discover the most likely pair. As shown in eq. 1, a total log-likelihood score ($LL$total) of each allele pair integrated the likelihoods of the observed genotype over individual SNP sites ($LL$geno) and the phase across multiple sites ($LL$phase), together with the probability of the allele pair present in human ($LL$freq).

$$LL_{total} = \Sigma LL_{geno}^{i} + \Sigma LL_{phase}^{i,i+1} + LL_{freq}, \ i \in SNP \text{ Sites at a given locus} \quad \text{(eq. 1)}$$

Based on a Bayesian model, the posterior log-likelihood $LL_{gene}^{i}$ was proportional to the conditional log-likelihood log $P(D^i|G^i)$, which was the log-probability of observing the piled up bases ($D^i$) given the genotype of the allele pair interested ($G^i$) at site i. The marginal prior log $P(G^i)$ was assumed constant for any genotype and therefore was removed. $P(D^i|G^i)$ was the product of individual conditional log-likelihoods of observing a base j at site i, $P(b^i_j|G^i)$ (eq. 2).

$$P(D^i | G^i) = \prod_j P(b^i_j | G^i), \quad \text{(eq. 2)}$$

$b^i_j$ = base of read $j$ at site $i$, $G^i = g^i_1 g^i_2$ $P(b^i_j | Gi) = 1 - q_j$ $\qquad = \frac{1-q_j}{2} + \frac{q_j/3}{2}$ $\qquad = q_j/3$ $g^i_1 = g^i_2 = b^i_j$ $g^i_1 \neq g^i_2$ and $b^i_j = g^i_1$ or $b^i_j = g^i_2$ $b^i_j \neq g^i_1$ and $b^i_j \neq g^i_2$ $q_i$ was the error rate converted from the Phred score of the base 3.

The phase likelihood over two adjacent SNP sites was modeled analogously to the genotype likelihood of one SNP site. With two sites, there were 15 possible mismatch (out-of-phase) states and 1 matching (in-phase) state, instead of 3 mismatches and 1 match for a single site. Specifically, $LL_{phase}^{i,i+1}$-was proportional to the log-probability of observing the pairs of bases on the same strand across two adjacent SNP sites i and t+1 ($D^{i,i+1}$) given the phase sequence of the allele pair interested at the two sites ($G^{i,i+1}$). There were 15 possible mismatch (out-of-phase) states and 1 matching (in-phase) state across two sites. $P(D^{i,i+1}|H^{i,i+1})$ was the product of the conditional log-likelihoods from all reads covering the site i and i+1 (eq. 3). $q_{err}$ was the out-of-phase error rate (0.01).

$$P(D^{i,i+1} | G^{i,i+1}) = \prod_j P(r_j^{i,i+1} | G^{i,i+1}) \quad \text{(eq. 3)}$$

$r_j^{i,i+1} = b^i_j b^{i+1}_j$, the pair of base on read $j$ at site $i$ and $i+1$ $G^{i,i+1} = (g^i_1 g_1^{i+1}, g^i_2 g_2^{i+1})$, $\qquad g^i_1 g_1^{i+1}$ and $g^i_2 g_2^{i+1}$ for allele 1 and 2, respectively $P(r_j^{i,i+1} | G^{i,i+1}) = 1 - q_{err}$ $g^i_1 g_1^{i+1} = g^i_2 g_2^{i+1} = b^i_j b^{i+1}_j = \frac{1 - q_{err}}{2} + \frac{q_{err}/15}{2}$ $\qquad g^i_1 g_1^{i+1} \neq g^i_2 g_2^{i+1}$, $b^i_j b^{i+1}_j = g^i_1 g_1^{i+1}$ or $b^i_j b^{i+1}_j = g^i_2 g_2^{i+1} = q_{err}/15$ $b^i_j b^{i+1}_j \neq g^i_1 g_1^{i+1}$ and $b^i_j b^{i+1}_j \neq g^i_2 g_2^{i+1}$ Eq. 3 avoided the bias to favor allele pairs with heterogeneous phase sequence ($g^i_1 g_1^{i+1}$, $g^i_2 g_2^{i+1}$), $g^i_1 g_1^{i+1} \approx g^i_2 g_2^{i+1}$ in previous work, induced by calculating a binomial probability based on the number of in-phase and out-of-phase reads. The in-phase read count for the heterogeneous phase is the sum of, and therefore always larger than, the in-phase read counts supporting the two homogeneous phases ($g^i_1 g_1^{i+1}$, $g^i_1 g_1^{i+1}$) and ($g^i_2 g_2^{i+1}$, $g^i_2 g_2^{i+1}$). Thus, the heterogeneous phase always has a higher probability than the two corresponding homogeneous phases in the binomial model. In contrast, the Bayesian model described herein favors a heterogeneous phase only with roughly balanced $g^i_1 g_1^{i+1}$ and $g^i_2 g_2^{i+1}$ reads, but not when one type predominates, which suggests a homogeneous phase after all.

The allele frequencies for the major class I and II loci were downloaded from the Allele Frequency Net. For each protein (four-digit) family, the maximum frequency from the documented alleles was used and shared by all the alleles within. A background value of 0.0001 was assigned to protein families (and alleles) with unknown frequency. $LL$freq was computed as the sum of the log-frequencies of the two alleles.

The pair of alleles with the highest $LL$total was reported as the predicted HLA type. In general, $LL$total was dominated by the $LL$gene and $LL$phase components. $LL$freq was significantly smaller by often a few orders of magnitude. Thus, although the implemented allele frequencies might be subjected to uncertainties, we expected no significant impact to the results.

Example 2

PHLAT Accurately Determines HLA Type Using Short Reads

To evaluate PHLAT with short reads, the HapMap transcriptome sequencing (RNAseq) dataset was used. Transcriptome profiling of lymphoblastoids using paired-end short reads (2×37 bp) were obtained from a public database for 60 Utah residents with ancestry from northern and western Europe from the HapMap project (study accession ERP000101). Fifty of these samples were genotyped at major class I and II HLA loci at four-digit resolution initially by de Bakker et al. *Nat. Genet.* 38:1166-1172 (2006) and subsequently validated using different techniques in Erlich et al., *BMC Genomics* 12:42 (2011). One sample (run accession ERR009139) was excluded due to an abnormally low rate of reads mappable to human genome (<20%). The remaining 49 subjects were used for analysis and comparisons in this work.

The HapMap RNAseq data employed paired-end 37 bp reads. Similar read lengths (~35 bp) were often used in transcriptome sequencing studies. However, they were within the low extreme of applicable read lengths. Using prior techniques, it has been difficult to accurately determine genotypes using such very short reads. The difficulties are augmented at the highly polymorphic HLA loci. Predictions of the four-digit HLA types using the HapMap RNAseq dataset with previous HLA typing methods have been inaccurate (FIG. 3). For example, the seq2HLA process was not suitable to resolve four-digit HLA types, with a low accuracy of 32% (Boegel et al., *Genome Med.* 4:102 (2013)). When HLAminer was applied to this dataset, it was only possible to execute the process in alignment mode, as its contig assembly mode did not work due to the short read length. The resulting accuracy was only 39.8% (FIG. 3). HLAforest reached a higher but still suboptimal prediction accuracy of 84.2% (FIG. 3).

Using the same HapMap RNAseq dataset, use of the PHLAT process of Example 1 inferred 96.2% of the four-digit HLA types correctly at the class I loci and 92.3% overall for both class I and II loci combined (FIG. 3). PHLAT also accurately predicted the homozygous calls. Among 45 homozygous loci (90 alleles) at four-digit resolution, merely 6 were mistyped to be heterozygous (total of 7 false alleles). A majority of the mistyped alleles were accurate at the two-digit resolution and differed from the true alleles by only one or two nucleotides.

In addition, PHLAT predicted two-digit HLA types more accurately than previous methods. PHLAT predicted only 5 of 564 two-digit alleles incorrectly (an accuracy of 99.1%), whereas the two-digit accuracy of previous HLA prediction processes was no higher than 97.3% for this dataset (FIG. 3).

PHLAT also provided an option to exclude very rare HLA alleles that did not have any record of population frequency at the Allele Frequency Net. With this option, the search for most likely HLA types was reduced to 2094 alleles at HLA-A (526), HLA-B(674), HLA-C(373), HLA-DQA1 (33), HLA-DQB1(81), HLA-DRB1(407) loci. Use of PHLAT under these conditions resulted in an accuracy of 93.0% at four-digit resolution when excluding rare alleles, comparable to the accuracy with rare alleles included (92.3%, see above).

Example 3

PHLAT Accurately Determines HLA Type Using Lower Coverage Sequencing Data

The HapMap whole exome sequencing (WXS) dataset and the accompanying class I four-digit HLA types were gathered from Utah residents with ancestry from northern and western Europe, Japan and Nigeria. The WXS data were obtained from a public database via study accessions SRP004078, SRR004076 and SRR004074, and the HLA genotypes were taken from Warren et al., *Genome Med.* 4:95 (2012) and Abecasis et al., *Nature* 467:1061-1073 (2010). The sequencing was processed by paired-end 101 bp reads, with a median coverage'-60× over the CDS regions of the HLA loci (also see Results).

PHLAT and other programs were evaluated using the 2×101 bp whole exome sequencing (WXS) data of 15 HapMap individuals from CEU, JPT and YRI populations. The read length was considerably longer than that of the HapMap RNAseq data. However, the sequencing depth was reduced. For the HLA loci interested, the post-mapping depth was—60×, whereas the HapMap RNAseq dataset had 330×. Although this fold coverage may be considered decent for general genotyping, it can be challenging for accurate typing of the highly polymophic HLA loci.

The performance of various HLA typing processes using the WXS dataset is provided in FIG. 3. The assembly mode of HLAminer was applied to the dataset as it delivered better results than the alignment mode, presumably because the contigs were more useful than individual reads in sequence alignment with the alleles and were less dependent of the coverage. At four-digit resolution, the accuracy of HLAminer was 53.3%,. HLAforest was also executed locally on the same dataset with default settings, resulting in an accuracy of 45.6%. The performance of HLAforest was poorer with the WXS dataset compared to the HapMap RNAseq dataset despite that the WXS data having much longer reads.

When the PHLAT process described in Example 1 was applied to the WXS data it resulted in a four-digit typing accuracy of 93.3%. In addition, PHLAT gave a two-digit accuracy of 95.6%, higher than seq2HLA (93.3% with no threshold on p-values) and considerably better than HLAminer (78.9%) and HLAforest (81.1%).

Example 4

Application of PHLAT to Targeted Amplicon Sequencing Data

Figure 4:
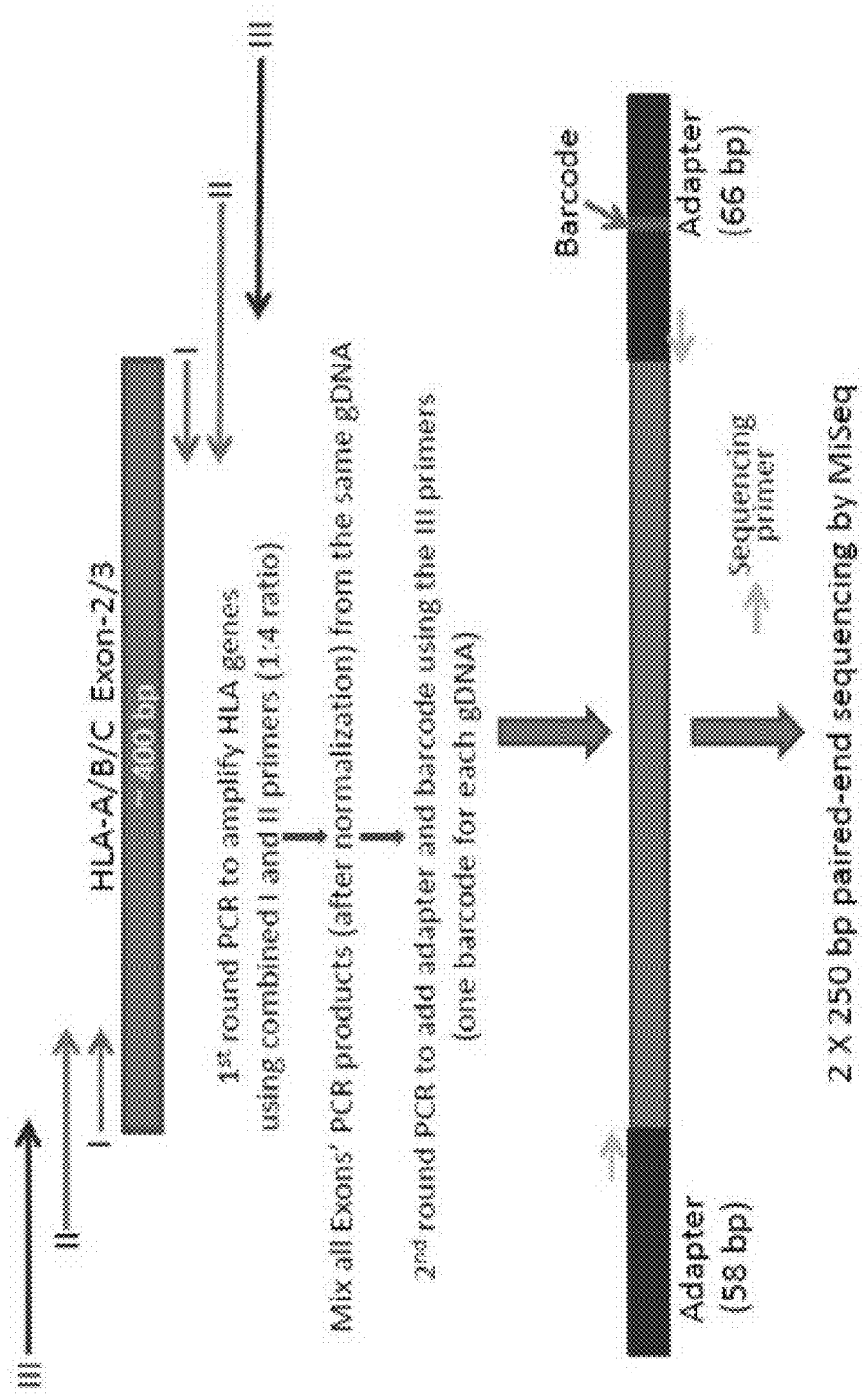
FIG. 4 is a schematic diagram depicting the targeted amplicon sequencing strategy used in Example 3 to generate the HLA sequence data for HLA typing.

The PHLAT process described in Example 1 was applied to targeted amplicon sequencing data. The data were generated by amplifying class I HLA-A and HLA-B loci in five human cell lines using a PCR amplification (FIG. 4). Briefly, in the first round of PCR, amplicons were generated for the exon 2 and 3 at HLA-A and B loci (primers sequences provided in FIG. 5) and Illumina sequencing adapters were added simultaneously. The four amplicons were pooled with a 1:1:1:1 ratio and barcoded using a second round of PCR. Finally, sequencing of pooled five samples was performed on an Illumina MiSeq (Illumina Inc. CA) by a multiplexed paired-end run with 2×250 cycles. De-multiplexed FASTQ files of the five samples were obtained by MiSeq Reporter software.

The HLA-A and B loci of the five samples were also genotyped by Sanger sequencing as follows. Genomic DNA was extracted from the above 5 cell lines by QIAamp® DNA Mini kit (Qiagen Inc. CA) at the concentration of 15-30 ng/nL, and subsequently PCR-amplified and purified using the SeCore Sequencing Kit (Life Technologies Inc., CA). The sequencing reactions were set up on the 3730×1 automated ABI sequencing instrument. The uTYPE® SBT software (Invitrogen Inc. CA) was used to process the sequence files and create the HLA typing report. Independent HLA typing of the five samples was executed by a commercial vendor (Life Technologies Inc., CA) and returned matching results.

The PHLAT process of Example 1 uses the Bowtie 2 aligner, which is capable of managing both short and long reads. PHLAT was tested on a paired-end 250 bp amplicon sequencing dataset of 5 samples. For a total of 20 experimentally validated alleles at HLA-A and HLA-B loci, PHLAT predicted the HLA type with 100% accuracy at both two-digit and four-digit resolutions (FIG. 3). With the exception of HLAminer, previously disclosed processes were not able to predict HLA type using this sequencing data. After running the assembly mode of HLAminer, obtained an accuracy of 50% and 95% for four-digit and two-digit resolution, respectively Example 5

Characterization of Mistyped Alleles

Figure 6:
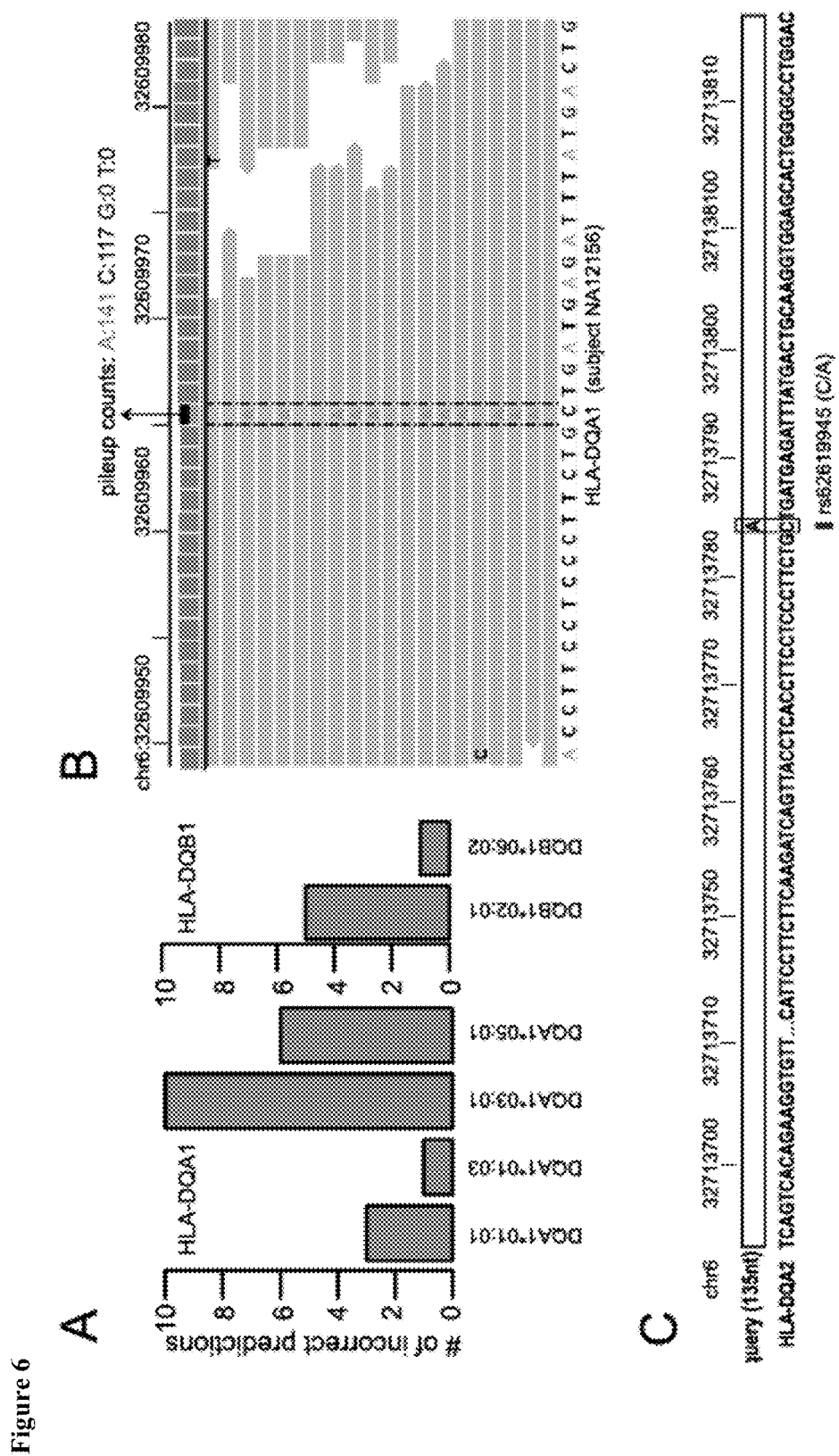
FIG. 6 includes three panels, identified as panels (A), (B) and (C). Panel (A) is a histogram that illustrates the type (x-axis) and the number (y-axis) of the misidentified alleles at the HLA-DQA1 (left panel) and HLA-DQB1 (right panel) loci, summarized over the HapMap RNAseq, the 1000 Genome WXS and the HapMap WXS datasets. Panel (B) is a diagram depicting the mapped reads in one representative sample, where the HLA-DQA1*03:01 allele is mistyped as the HLA-DQA1*03:03 allele. The mapped reads are shown around the single SNP position (chr6: 32609965, highlighted in between two vertical dashed lines) that distinguishes the two alleles. The hg19 reference sequence of the HLA-DQA1 gene is shown at the bottom of the panel. The pileup counts of the A, C, G, T bases at the highlighted SNP are 141, 117, 0 and 0, respectively. Panel (C) is a diagram depicting the alignment of a 135-nucleotide segment from the HLA-DQA1*03:03 allele, noted as the query, with the HLA-DQA2 reference sequence in human genome hg19. The query sequence is simplified as a horizontal bar with only the mismatches indicated. The existing dbSNP record at the mismatch is labeled with a red vertical marker and the associated identification numbers (e.g. rs62619945) followed by a parenthesis indicating the major and the alternative base sequences. The alignment of the SNP that differ the DQA1*03:01 and DQA1*03:03 alleles is boxed. Nucleotides 1-18 of HLA-DQA2 shown in the figure represent SEQ ID NO:24 (TCAGTCACAGAAGGTGTT) while the remaining nucleotides represent SEQ ID NO:25 (CATT . . . GGAC).

Mistyped four-digit alleles in PHLAT are collected from the HapMap RNAseq, 1000 Genome WXS and the HapMap WXS datasets, and are summarized per allele type (FIG. 6A). It was investigated whether certain allele types were enriched, and if so, whether the algorithm or other reasons introduce them. At the HLA-A, B, C and DRB1 loci, almost all the alleles had a limited sample size (<10 total occurrences) and mistyping incidents (<2). Thus, there was no apparent enrichment for allele type.

At the HLA-DQA1 and HLA-DQB1 loci, a few specific alleles dominate the observed prediction errors. As shown in FIG. 6A, among a total of twenty faulty predictions at HLA-DQA1, ten HLADQA1*03:01 alleles are typed as HLA-DQA1*03:03, and six HLA-DQA1*05:01 alleles are mistaken as HLADQA1*05:05. At the HLA-DQB1 locus, five HLA-DQB1*02:01 alleles are called as HLA-DQB1*02:02. These errors account for >80% of all false predictions at the HLA-DQA1 and HLA-DQB1 loci. These alleles also exhibit low prediction accuracies in this study (61.5%-73.7%). Although the real and predicted alleles are highly homologous in sequence (<=3 SNPs), a few observations below suggest that these errors may not be random.

Other algorithms, HLAforest and HLAminer, exhibit a similar tendency to mistype DQA1*03:01 as DQA1*03:03 in the same samples miscalled by PHLAT. HLAforest makes identical errors as PHLAT in seven samples. The output from HLAminer, DQA1*03:01P, is a P-designation annotation that groups DQA1*03:01, DQA1*03:03 and a few other alleles. Rerun of HLAminer without the P-designation reveals that DQA1*03:03 is the most confident prediction in all the samples mistyped by PHLAT. As the same mistakes occur in the algorithms that implement different aligners, e.g. Bowtie 2 for PHLAT, Bowtie for HLAforest and BWA for HLAminer, the errors are not caused by a specific alignment engine. Indeed, changing the aligner to BWA in PHLAT does not alter the output in any affected sample. These results suggest that the problem may not be due to the computational strategy or aligner choice in the algorithm.

The DQA1*03:03 inference is supported by a decent amount of reads in all cases. FIG. 6B illustrates the read mapping details around the single SNP site differentiating the DQA1*03:01 and DQA1*03:03 alleles (chr6: 32609965, base A for DQA1*03:03 and C for DQA1*03:01) in one representative sample where such a mistyping occurs (subject NA12156). The second allele in this samples is DQA1*02:01, whose sequence is C at this position. These reads have passed through the PHLAT pipeline and are used for the HLA prediction. In sample NA12156, about half of the bases are A's, resulting in a heterozygous genotype of AC. Hence, inferring a DQA1*03:03 allele, together with a DQA1*02:01 allele, is convincing given the data. Similar observations hold for all other samples with DQA1*03:03 predictions. It suggests that the errors may not be simply due to random noise in the data.

It is possible that the reads supporting the alternative allele are originated from elsewhere in the genome. A BLAST query using a 135-nucleotide segment (chr6: 32609874-32610008) harboring the SNP site (chr6: 32609965) from the HLA-DQA1*03:03 allele returns the top full length hit located at the exon 3 of the HLADQA2 gene. There is no other mismatch except the very SNP site between the two alleles within this region (FIG. 6C). IMGT database does not include any HLADQA2 entry due to the limited knowledge of its alleles. Consequently, all previous algorithms have no HLADQA2 sequence in their mapping reference. PHLAT extends the reference to the whole genome. Yet it only includes the sequence of one specific HLA-DQA2 allele used in the hg19 genome and thereby not fully capturing its polymorphisms either. Given the high sequence homology and the lack of complete allelic references of HLA-DQA2, misaligning the reads of the HLA-DQA2 gene to the HLA-DQA1 gene is a non-negligible possibility. In fact, there is a common C-to-A missense SNP of the HLA-DQA2 gene (rs62619945, —4% minor allele frequency, FIG. 6C) at chr6: 32713784, the matching site in the sequence alignment for the DQA1*03:03 allelic SNP. Thus, if a subject happens to carry a specific HLA-DQA2 allele with the rs62619945 SNP, the resulting reads may be falsely taken as from an HLA-DQA1*03:03 allele.

Analogous observations exist for other two frequently mistyped alleles, HLA-DQA1*05:01 and HLA-DQB1*02:01. PHLAT, HLAminer and HLAforest (without P-designation) all misidentify them as HLA-DQA1*05:05 and HLA-DQB1*02:02, respectively, in five samples. There are three SNPs driving the DQA1*05:05 calls at chr6: 32605266, chr6: 32610002 and chr6: 32610445. Each SNP has a significant number of mapped reads supporting the DQA1*05:05 allele. Further, each SNP is located within an exon segment (sequence taken from the DQA1*05:05 allele) homologous to the HLA-DQA2 gene. These segments are of 72-116 nucleotides in length and differ from the HLA-DQA2 sequence (hg19 genome) at 2-4 chromosomal positions. All the positions in the HLA-DQA2 gene have a dbSNP record wherein the alternative base matches the sequence in the DQA1*05:05 allele. Thus, it is possible to confuse the reads from the HLA-DQA2 and HLA-DQA1 loci regarding to these regions. Similarly, the SNP favoring the HLADQB1*02:02 allele over the HLA-DQB1*02:01 allele (chr6: 32629905). It is inside a homologous region of 91 nucleotides between the HLA-DQB1 and HLA-DQB2 genes. HLA-DQB2 alleles are poorly studied and not recorded in IMGT database either.

Collectively considering the results above, we reason that misaligning the reads from the minor HLA-DQA2 and DQB2 loci to their homologous major HLA-DQA1 and DQB1 loci, respectively, may have led to the unusual high frequency of the mistyped HLA-DQA1 and DQB1 alleles. This limitation is independent of the algorithms. Incorporating the allelic sequences of HLA-DQA2 and DQB2 in the mapping reference will likely alleviate the problem. Mistyped alleles is less a concern when using data with paired-end reads of 100 bp or longer, as the homologous regions discussed here are around 100 nucleotides. Long sequencing reads may extend into surrounding less homologous regions to reduce the misalignment. Users of PHLAT or other existing algorithms can validate HLADQA1*03:03, HLA-DQA1*05:05 and HLA-DQB1*02:02 allele types by Sanger or targeted amplicon sequencing.

Example 6

Factors Influencing the Accuracy of HLA Inference

The PHLAT HLA prediction outcomes from the datasets described above were compiled to systematically investigate how the sequencing parameters impacted the accuracy of HLA inference. The benchmarking datasets offered test cases over a wide range of read length (37 bp-250 bp) and depth (from <60× to >1000×) as well as different sequencing protocols (paired-end or used as single-end).

Figure 2:
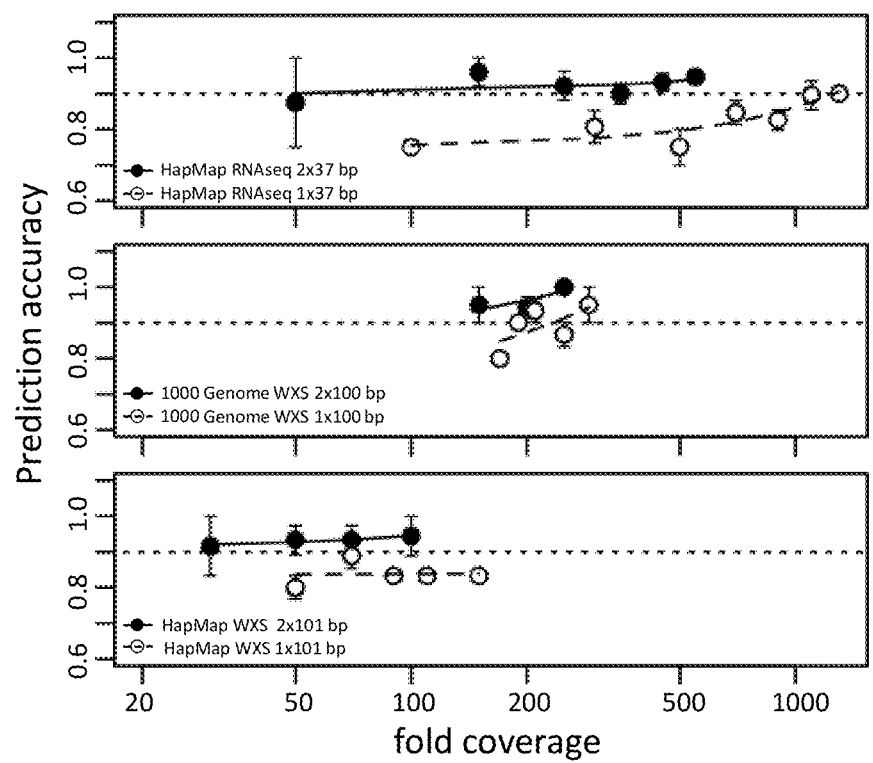
FIG. 2 is a graph illustrating the impact of read length, coverage and sequencing protocols on HLA typing accuracy. The plot includes samples from the HapMap RNAseq (37 bp read length), the Genome WXS (100 bp length), and the HapMap WXS (101 bp read length) datasets. Prediction accuracies considering input data as paired-end (close symbols and solid lines) and single-end (open symbols and dashed lines) are illustrated. The symbols represent the mean accuracy at four-digit resolution of the samples that are binned by their fold coverage of the HLA loci, with the error bars indicating the variance. The post-mapping fold coverage is calculated regarding the CDS regions of the major class I and II HLA loci, excluding the reads suboptimal or not aligned to the candidate alleles. The smooth lines were derived by spline interpolation to illustrate the trend of the symbols.

FIG. 2 illustrated the results from three datasets: the HapMap RNAseq, 1000Genome WXS and HapMap WXS. The HapMap RNAseq and HapMap WXS datasets are described in examples 2 and 3.

For each dataset, the samples were binned by their post-mapping fold coverage at the HLA loci (x-axis). The y-coordinates of the symbols represented the mean accuracy (at four-digit resolution) of the samples within each bin, with error bars indicating the variance. For each paired-end sequencing dataset (closed symbols), the samples were also processed under the single-end assumption (open symbols) by ignoring the paired relationship between the reads. The trend of the symbols was illustrated by the smooth lines derived via spline interpolation.

As shown in FIG. 2, the accuracy of the PHLAT process positively correlated with the fold coverage. The ascending trend of accuracy with increasing fold coverage occurred not only within individual datasets but also in between them. For example, the 1000Genome WXS samples that had systematically higher coverage than the HapMap WXS samples consistently exhibited higher accuracies, despite other sequencing parameters of the two datasets were similar. This dependency might help estimate an empirical coverage threshold for PHLAT to reach optimal predictions. To achieve accuracy of no less than 90% (dashed horizontal line, FIG. 2) in paired-end sequencing, 30×-50× coverage might be applied, with >100× for read length below 100 bp.

When the paired constrains were ignored and the reads treated as single-ended, a non-negligible systematic decrease in the prediction accuracy was observed for all datasets. In FIG. 2, the accuracy of HapMap WXS data dropped from >90% to —85% for paired-end (2×101 bp, bottom panel, close circles) and single-end (1×101 bp, bottom panel, open circles) reads, respectively. The decrease was more dramatic in the HapMap RNAseq data: from 90-95% (2×37 bp, top panel, close circles) to 70-90% (1×37 bp, top panel, open circles). These observations highlighted the importance of paired-end sequencing for HLA type inferences. The advantage of paired reads originated from the effectively doubled read length that reduced the mapping ambiguity. In addition, the long end-to-end span (usually a few hundred of bases) linked SNPs that were relatively far apart, allowing PHLAT to utilize the phase information from SNP pairs over a long range.

We claim:

1. A computer-implemented method comprising:

performing a nucleic acid amplification process that produces an amplification product that comprises a nucleic acid sequence of a locus of a subject, wherein the locus comprises one or more single nucleotide polymorphisms (SNPs);

performing a sequencing process on the amplification product that produces a plurality of sequencing reads, wherein the plurality of sequencing reads is comprised of sequencing reads of 35-100 base pairs;

mapping the plurality of sequencing reads to a reference sequence comprising a genome sequence and a plurality of allele sequences of a locus to identify pairs of candidate alleles;

for each pair of candidate alleles, determining genotype log-likelihood scores for each individual SNP in the locus, each genotype log-likelihood score being a sum of the log-probabilities for each individual SNP in the locus that the pair of candidate alleles could account for sequences present at the individual SNP in the sequencing reads that map to the SNP;

for each pair of candidate alleles, determining phase log-likelihood scores for each sequential pair of SNPs in the locus, each phase log-likelihood score being a sum of the log-probabilities for each sequential pair of SNPs in the locus that the pair of candidate alleles could account for sequences present at the sequential pair of SNPs in the sequencing reads that map to the sequential pair of SNPs;

for each pair of candidate alleles, determining a frequency log-likelihood score, the frequency log-likelihood score being a sum of the log-frequencies at which each of the pair of candidate alleles are present in the human population; and selecting a pair of candidate alleles for which the sum of the genotype log-likelihood score, the phase log-likelihood score and the frequency log-likelihood score is highest as the alleles present at the locus.

2. The method of claim 1, wherein the genome sequence is a human genome sequence and the plurality of allele sequences are human sequences.

3. The method of claim 2, wherein the sequence of the locus in the genome sequence has been removed or masked.

4. The method of claim 2, wherein the human genome sequence is GRCh37/hg19.

5. The method of claim 1, wherein mapping further comprises:
identifying as a first set of candidate alleles the alleles to which map the greatest number of sequencing reads;
identifying as a second set of candidate alleles the alleles to which map the greatest number of sequencing reads, excluding the sequencing reads that map to the first set of candidate alleles; and
if less than 90% of the sequencing reads that map to the locus map to an allele of the first or second set of candidate alleles, identifying as a third set of candidate alleles the alleles to which map the greatest number of sequencing reads, excluding the reads that map to the first or second set of candidate alleles.

6. The method of claim 1, wherein the plurality of allele sequences are selected from a set of protein groups.

7. The method of claim 5, wherein, if the number of sequencing reads that map to the locus following exclusion of the sequencing reads that map to the first set of candidate alleles is greater than 1% of the number of sequencing reads that map to the first set of candidate alleles, further identifying as a subset of the second set of candidate alleles the alleles to which map the second greatest number of sequencing reads without excluding the sequencing reads that map to the first set of candidate alleles.

8. The method of claim 5, wherein the third set of candidate alleles are only identified if the number of sequencing reads that map to the alleles to which map the greatest number of sequencing reads, excluding the reads that map to the first or second set of candidate alleles, make up at least 10% of the total number of sequencing reads that map to the locus.

9. The method of claim 1, further comprising receiving sequence data, the sequence data comprising the plurality of sequencing reads, wherein the sequence data comprises genome-wide sequencing data.

10. The method of claim 9, wherein the genome-wide sequencing data are transcriptome sequencing data, whole exome sequencing data, or whole genome sequencing data.

11. The method of claim 10, wherein the coverage of the sequence data is at least 30 fold.

12. The method of claim 10, wherein the coverage of the sequence data ranges from 30 fold to 100 fold, and wherein the plurality of sequencing reads are from DNA.

13. The method of claim 10, wherein the coverage of the sequence data ranges from 100 fold to 500 fold, and wherein the plurality of sequencing reads are from RNA.

14. The method of claim 10, wherein the coverage of the sequence data is at least 1000 fold, and the plurality of sequencing reads are from targeted sequence.

15. The method of claim 1, wherein the plurality of sequencing reads are paired-end reads.

16. The method of claim 1, wherein the plurality of sequencing reads are single-end reads.

17. The method of claim 1, wherein the locus is a highly polymorphic locus.

18. The method of claim 1, wherein the genome sequence comprises transcriptome sequences, whole exome sequences, or whole genome sequences.

19. A computer readable medium storing processor-executable instructions adapted to cause one or more computing devices to:
perform a nucleic acid amplification process that produces an amplification product that comprises a nucleic acid sequence of a locus of a subject, wherein the locus comprises one or more single nucleotide polymorphisms (SNPs);
perform a sequencing process on the amplification product that produces a plurality of sequencing reads, wherein the plurality of sequencing reads is comprised of sequencing reads of 35-100 base pairs;
map the plurality of sequencing reads to a reference sequence comprising a genome sequence and a plurality of allele sequences of a locus to identify pairs of candidate alleles;
for each pair of candidate alleles, determine genotype log-likelihood scores for each individual SNP in the locus, each genotype log-likelihood score being a sum of the log-probabilities for each individual SNP in the locus that the pair of candidate alleles could account for sequences present at the individual SNP in the sequencing reads that map to the SNP;
for each pair of candidate alleles, determine phase log-likelihood scores for each sequential pair of SNPs in the locus, each phase log-likelihood score being a sum of the log-probabilities for each sequential pair of SNPs in the locus that the pair of candidate alleles could account for sequences present at the sequential pair of SNPs in the sequencing reads that map to the sequential pair of SNPs;
for each pair of candidate alleles, determine a frequency log-likelihood score, the frequency log-likelihood score being a sum of the log-frequencies at which each of the pair of candidate alleles are present in the human population; and
select a pair of candidate alleles for which the sum of the genotype log-likelihood score, the phase log-likelihood score and the frequency log-likelihood score is highest as the alleles present at the locus.

20. An apparatus comprising:

one or more processors; and a memory comprising processor executable instructions that, when executed by the one or more processors, cause the apparatus to:

perform a nucleic acid amplification process that produces an amplification product that comprises a nucleic acid sequence of a locus of a subject, wherein the locus comprises one or more single nucleotide polymorphisms (SNPs);

perform a sequencing process on the amplification product that produces a plurality of sequencing reads, wherein the plurality of sequencing reads is comprised of sequencing reads of 35-100 base pairs;

map the plurality of sequencing reads to a reference sequence comprising a genome sequence and a plurality of allele sequences of a locus to identify pairs of candidate alleles;

for each pair of candidate alleles, determine genotype log-likelihood scores for each individual SNP in the locus, each genotype log-likelihood score being a sum of the log-probabilities for each individual SNP in the locus that the pair of candidate alleles could account for sequences present at the individual SNP in the sequencing reads that map to the SNP;

for each pair of candidate alleles, determine phase log-likelihood scores for each sequential pair of SNPs in the locus, each phase log-likelihood score being a sum of the log-probabilities for each sequential pair of SNPs in the locus that the pair of candidate alleles could account for sequences present at the sequential pair of SNPs in the sequencing reads that map to the sequential pair of SNPs;

for each pair of candidate alleles, determine a frequency log-likelihood score, the frequency log-likelihood score being a sum of the log-frequencies at which each of the pair of candidate alleles are present in the human population; and select a pair of candidate alleles for which the sum of the genotype log-likelihood score, the phase log-likelihood score and the frequency log-likelihood score is highest as the alleles present at the locus.

21. The method of claim 1, wherein the alleles present at the locus comprise an HLA type at the locus.

22. The method of claim 21, wherein the sample is taken from a cell to be transplanted into a subject, and further comprising determining if an HLA type of the subject matches the HLA type at the locus.

23. The method of claim 22, further comprising transplanting the cell into the subject if the HLA type of the subject matches the HLA type at the locus.

24. The method of claim 22, further comprising:

transplanting the cell into the subject if the HLA type of the subject matches the HLA type at the locus; and administering an agent that reduces the likelihood of transplant rejection to the subject.

* * * * *

SEQUENCE LISTING

<160> NUMBER OF SEQ ID NOS: 25

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
crggtctcag ccactsctc                                                  19

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctcggacccg gagactgt                                                   18

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3 ctyggggac ygggctgac                                                   19

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cccaattgtc tccctcctt g                                              21

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggsagggaaa tggcctct                                                 18

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggatggggag tcgtgacct                                                19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcgtttaccc ggtttcatt                                                19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cggcgaccta taggagatgg                                               20

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(26)
<223> OTHER INFORMATION: a, c, t, g, unknown or other

<400> SEQUENCE: 9
ctacacgacg ctcttccgat ctnnnncrgg tctcagccac tsctc        45

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cagacgtgtg ctcttccgat ctctcggacc cggagactgt        40

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(26)
<223> OTHER INFORMATION: a, c, t, g, unknown or other

<400> SEQUENCE: 11
ctacacgacg ctcttccgat ctnnnnctyg ggggacyggg ctgac        45

<210> SEQ ID NO 12
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cagacgtgtg ctcttccgat ctcccaattg tctccctcc ttg        43

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(26)
<223> OTHER INFORMATION: a, c, t, g, unknown or other

<400> SEQUENCE: 13
ctacacgacg ctcttccgat ctnnnnggsa gggaaatggc ctct        44

<210> SEQ ID NO 14
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cagacgtgtg ctcttccgat ctggatgggg agtcgtgacc t        41

<210> SEQ ID NO 15

```
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(26)
<223> OTHER INFORMATION: a, c, t, g, unknown or other

<400> SEQUENCE: 15
ctacacgacg ctcttccgat ctnnnngcgt ttacccggtt tcatt             45

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cagacgtgtg ctcttccgat ctcggcgacc tataggagat gg                42

<210> SEQ ID NO 17
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aatgatacgg cgaccaccga gatctacact ctttccctac acgacgctct tccgatct    58

<210> SEQ ID NO 18
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
caagcagaag acggcatacg agatgattag ccgtgactgg agttcagacg tgtgctcttc    60
cgatct                                                               66

<210> SEQ ID NO 19
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
caagcagaag acggcatacg agattgcgac atgtgactgg agttcagacg tgtgctcttc    60
cgatct                                                               66

<210> SEQ ID NO 20
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 20
caagcagaag acggcatacg agatcagcgt tagtgactgg agttcagacg tgtgctcttc    60
cgatct                                                                66

<210> SEQ ID NO 21
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caagcagaag acggcatacg agattccgta aggtgactgg agttcagacg tgtgctcttc    60
cgatct                                                                66

<210> SEQ ID NO 22
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
caagcagaag acggcatacg agatatggta ccgtgactgg agttcagacg tgtgctcttc    60
cgatct                                                                66

<210> SEQ ID NO 23
<211> LENGTH: 35
<212> TYPE: DNA
<213> ORGANISM: Homo sapiens

<400> SEQUENCE: 23
accttcctcc cttctgctga tgagatttat gactg                                35

<210> SEQ ID NO 24
<211> LENGTH: 18
<212> TYPE: DNA
<213> ORGANISM: Homo sapiens

<400> SEQUENCE: 24
tcagtcacag aaggtgtt                                                   18

<210> SEQ ID NO 25
<211> LENGTH: 87
<212> TYPE: DNA
<213> ORGANISM: Homo sapiens

<400> SEQUENCE: 25
cattccttct tcaagatcag ttacctcacc ttcctccctt ctgctgatga gatttatgac    60
tgcaaggtgg agcactgggg cctggac                                         87
```